United States Patent [19]
Bekkaoui et al.

[11] Patent Number: 6,136,533
[45] Date of Patent: Oct. 24, 2000

[54] ADDITIVES FOR USE IN CYCLING PROBE REACTIONS

[75] Inventors: Faouzi Bekkaoui, Burnaby; Zora D. Modrusan, Vancouver; Isabelle A. Piche, Swift Current; Peter D. Duck, Burnaby; Lynn P. Cloney, Vancouver; Alfred C. K. Wong, Burnaby, all of Canada

[73] Assignee: ID Biomedical, Bothell, Wash.

[21] Appl. No.: 09/109,957

[22] Filed: Jul. 2, 1998

Related U.S. Application Data

[60] Provisional application No. 60/052,721, Jul. 3, 1997, provisional application No. 60/090,274, Jun. 22, 1998, and provisional application No. 60/086,026, May 18, 1998.

[51] Int. Cl.[7] .............................. C12Q 1/68; C12P 19/34
[52] U.S. Cl. .............................................. 435/6; 435/91.1
[58] Field of Search ..................... 435/6, 91.1; 536/24.3, 536/25.1; 530/350

[56] References Cited

U.S. PATENT DOCUMENTS

| | | | |
|---|---|---|---|
| 4,876,187 | 10/1989 | Duck et al. | 435/6 |
| 5,011,769 | 4/1991 | Duck et al. | 435/6 |
| 5,403,711 | 4/1995 | Walder et al. | 435/6 |
| 5,660,988 | 8/1997 | Duck et al. | 435/6 |
| 5,731,146 | 3/1998 | Duck et al. | 435/6 |

FOREIGN PATENT DOCUMENTS

| | | | |
|---|---|---|---|
| 229 701 B1 | 7/1987 | European Pat. Off. | |
| WO 95/05480 | 2/1995 | WIPO . | |
| WO 9612824 | of 1996 | WIPO | 435/6 |
| WO 96/08582 | 3/1996 | WIPO . | |
| WO 97/11199 | 3/1997 | WIPO . | |

OTHER PUBLICATIONS

Duck et al., "Probe Amplifier System Based on Chimeric Cycling Oligonucleotides," *BioTechniques* 9(2): 142–147, 1990.

Modrusan et al., "Spermine–mediated improvement of cycling probe reaction," *Molecular and Cellular Probes* 12: 107–116, 1998.

Pingoud et al., "Effect of Polyamines and Basic Proteins on Cleavage of DNA by Restriction Endonucleases," *Biochemistry* 23: 5697–5703, 1984.

Wetmur, "DNA Probes: Applications of the Principles of Nucleic Acid Hybridization," *Critical Reviews in Biochemistry and Molecular Biology* 26(3/4): 227–259, 1991.

Altwegg, "General problems associated with diagnostic applications of amplification methods," *Journal of Microbiological Methods* 23: 21–30, 1995.

Carrino and Lee, "Nucleic acid amplification methods," *Journal of Microbiological Methods* 23: 3–20, 1995.

Germann and Telenti, "Nucleic acid amplification methods in diagnostic virology," *Journal of Microbiological Methods* 23: 31–39, 1995.

Kitchin et al., "Avoidance of false positives," *Nature* 344: p. 201, 1990.

Kwok and Higuchi, "Avoiding false positives with PCR," *Nature* 339: 237–238, 1989.

Niederhauser et al., "Reliability of PCR Decontamination Systems," *PCR Methods and Applications* 4(2): 117–123, 1994.

*Primary Examiner*—Lisa B. Arthur
*Assistant Examiner*—Jehanne Souaya
*Attorney, Agent, or Firm*—Seed Intellectual Property Law Group

[57] ABSTRACT

A method for detecting a target nucleic acid molecule is provided, comprising the steps of (a) reacting a mixture comprising (i) a target nucleic acid molecule; (ii) a single-stranded nucleic acid probe containing a scissile linkage; (iii) an enzyme capable of cleaving the probe portion of a double-stranded target-probe complex at the scissile linkage; and (iv) ribosomal protein and/or spermine, under conditions and for a time sufficient to allow the target nucleic acid and probe to hybridize to each other and form a double-stranded target-probe complex, followed by cleavage of the probe and cycling of the target to a new uncleaved probe, such that one or more portions of the cleaved nucleic acid probe are released from the target-probe complex; and (b) determining whether cleaved portions of the nucleic acid probe are produced, and thereby detecting the presence of the target nucleic acid.

17 Claims, 9 Drawing Sheets

ADDITIVES FOR USE IN CYCLING PROBE REACTIONS

This application claims benefit of Provisional Appl. 60/052,721 filed Jul. 3, 1997 and Provisional Appl. 60/090, 274 filed Jun. 22, 1998, and Provisional Appl. 60/086,026 filed May 18, 1998.

TECHNICAL FIELD

The present invention relates generally to methods of detecting a target nucleic acid sequence, and more specifically, to the use of additives in cycling probe reactions which decrease the background caused by heterologous DNA.

BACKGROUND OF THE INVENTION

A wide variety of diagnostic techniques are presently available for detection of organisms within a biological sample, including for example, biochemical tests, immunological tests and cytological tests. The majority of these techniques, however, have drawbacks related to length of time, quantity of sample required, labor, training in the use of equipment, expertise level and lack of specificity or sensitivity of detection. Often the biological samples of interest may be limited in terms of the number of cells or quantity of target nucleic acid to be detected, which in turn will affect the sensitivity of the method used. Thus, for successful detection of an organism, it may be necessary to increase or amplify the quantity of target nucleic acids in order to overcome the sensitivity limitation of a small number of target organisms.

One of the most widely used in vitro methods for amplifying selected nucleic acid sequences is the Polymerase Chain Reaction ("PCR", see, e.g., U.S. Pat. Nos. 4,683,195 and 4,683,202). Briefly, two oligonucleotide primers which flank the DNA segment of the target sequence to be amplified are used to initiate exponential copying of the target sequence. After heat denaturation of the target, hybridization of the primers occurs to their complementary sequences on the opposite strands and replication occurs enzymatically due to elongation of the two primers. Repetitive cycles of denaturation, primer annealing, and extension are carried out, resulting in replication of a complementary strand to each of the original strands per cycle. In turn, each of the product strands is capable of being hybridized to the primers. This results in an exponential amplification of the target nucleic acid which can subsequently be detected.

There are, however, a number of technical problems associated with PCR. For example, false positive results can occur from contaminating nucleic acids arising from a number of sources (Kwok and Higuchi, *Nature* 339:237–238, 1989; Kitchin et al., *Nature* 344:201). PCR products from previous amplification of the target can also accumulate in the laboratory, resulting in cross-contamination between different samples. Problems can also arise from the co-amplification of non-specific target caused by hybridization of primers to extraneous sequences along the target template or other heterologous nucleic acids present in the sample. The problem of false negatives is discussed by Niederhauser et al. *PCR Methods Appl.* 4: 117–123, 1994. The technical ability of laboratory personnel, laboratory capabilities and logistics also have to be taken into consideration.

Problems with heterologous nucleic acid contamination, which may cause inhibition, or cross-over contamination, which gives false positive, affects other amplification technologies such as Nucleic Acid Sequence Based Amplification (NASBA), Gap Ligase Chain Reaction (Gap-LCR), Strand Displacement Amplification (SDA), and Q-Beta Replicase (See generally Carrino and Lee, *J. Microbiol. Meth.* 23:3–20, 1995; Altwegg, *J. Microbiol. Meth.* 23:21–30).

A number of these problems can be resolved if, in an amplification system, the target is not amplified. One such method is the cycling probe technology ("CPT", see, e.g., U.S. Pat. Nos. 5,011,769 and 5,403,711), where a specific probe containing a scissile linkage oligonucleotide complementary to the target sequence is utilized.

The present invention discloses novel compositions and methods for use in cycling probe reactions, which are simple, rapid and inexpensive to use. In particular, unlike other nucleic acid amplification technologies, the methods provided herein may be accomplished at a constant temperature, do not require more than one enzyme or probe and can be carried out in the presence of heterologous DNA that may be present in the sample. Further, the present invention provides other related advantages.

SUMMARY OF THE INVENTION

Briefly stated, the present invention provides compositions and methods for detecting target nucleic acid molecules utilizing a nucleic acid reaction which involves hybridization of one or more nucleic acid probes or specifically selected nucleic acid molecules to a nucleic acid target. Such methods generally comprise the steps of (a) reacting (i) one or more selected nucleic acid molecules (e.g., a probe, primer, or a series of probes), (ii) a sample which may contain the target nucleic acid molecule to be detected, and (iii) any one or more of (I) ribosomal protein, (II) spermine, and/or (III) a detergent and a chelator, under conditions and for a time sufficient to allow the selected nucleic acid molecule the opportunity to hybridize to the target nucleic acid molecule, and (b) determining whether hybridization occurs, and thereby detecting the presence of the target nucleic acid molecule.

Within one aspect of the invention, methods are provided for detecting a target nucleic acid molecule comprising the steps of (a) reacting a mixture comprising (i) a target nucleic acid molecule; (ii) a single-stranded nucleic acid probe containing a scissile linkage; (iii) an enzyme capable of cleaving the probe portion of a double-stranded target-probe complex at the scissile linkage; and (iv) ribosomal protein and/or spermine, and/or a detergent and a chelator, under conditions and for a time sufficient to allow the target nucleic acid and probe to hybridize to each other and form a double-stranded target-probe complex, followed by cleavage of the probe and cycling of the target to a new uncleaved probe, such that one or more portions of the cleaved nucleic acid probe are released from said target-probe complex; and (b) determining whether cleaved portions of the nucleic acid probe are produced, and thereby detecting the presence of the target nucleic acid.

Within various embodiments, determination of whether cleaved probe is produced can be accomplished by directly detecting cleaved portions of the nucleic acid probe, and/or detecting a decrease in the amount of uncleaved probe.

Within another aspect of the present invention, methods are provided for detecting the presence of a target nucleic acid sequence through hybridization with a substantially complementary nucleic acid probe, in which the probe:target nucleic acid sequence ratio is amplified through recycling of the target nucleic acid sequence, comprising the steps of (a) hybridizing a target nucleic acid sequence to a nucleic acid probe in the presence of ribosomal protein and/or spermine, to provide a probe:target nucleic acid sequence duplex; (b) cleaving only the probe within the probe:target nucleic acid sequence duplex with an enzyme which causes selective probe cleavage resulting in duplex disassociation, leaving the target nucleic acid sequence intact; (c) recycling of the target nucleic acid sequence by repeating steps (a) and (b); and (d) detecting cleaved probe, and thereby determining the presence of said target nucleic acid sequence.

Within various embodiments of the invention, the probe comprises the structure $[NA_1\text{-}S\text{-}NA_2]_n$, wherein $NA_1$ and $NA_2$ are different, non-complementary nucleic acid sequences (e.g., DNA), and S is a scissile linkage (e.g., "R," an RNA sequence). Within further embodiments, the enzyme is RNase H, and may be either thermostable (e.g., from *T. thermophilus*) or non-thermostable (e.g., from *E. coli*). A wide variety of ribosomal proteins may be utilized within the present invention, including both prokaryotic and eukaryotic ribosomal protein. Within preferred embodiments the ribosomal protein is S19 or L34 ribosomal protein.

Within yet further embodiments of the invention, the reaction mixture may further comprise spermine and/or a detergent (e.g., DTAB or CTAB) and/or a chelator (e.g., such as EGTA, EDTA, or a divalent cation such as $Mg^{++}$, $Mn^{++}$ or $Ca^{++}$), or alternatively, a detergent and/or a chelator.

Within further variants, the probe(s) and target nucleic acid molecule which are utilized in the hybridization reactions described herein need not be perfectly complementary, and indeed, may be purposely different by one, two, three or more nucleotides nucleic acids (see, e.g., PCT Publication WO 95/14106 and U.S. Pat. No. 5,660,988). Within further variants, the target nucleic acid molecule is present in a heterogeneous population of genomic nucleic acids.

These and other aspects of the present invention will become evident upon reference to the following detailed description and attached drawings. In addition, various references are set forth herein which describe in more detail certain procedures or compositions (e.g., plasmids, etc.), and are therefore incorporated by reference in their entirety.

DETAILED DESCRIPTION OF THE INVENTION

Definitions

Figure 1:
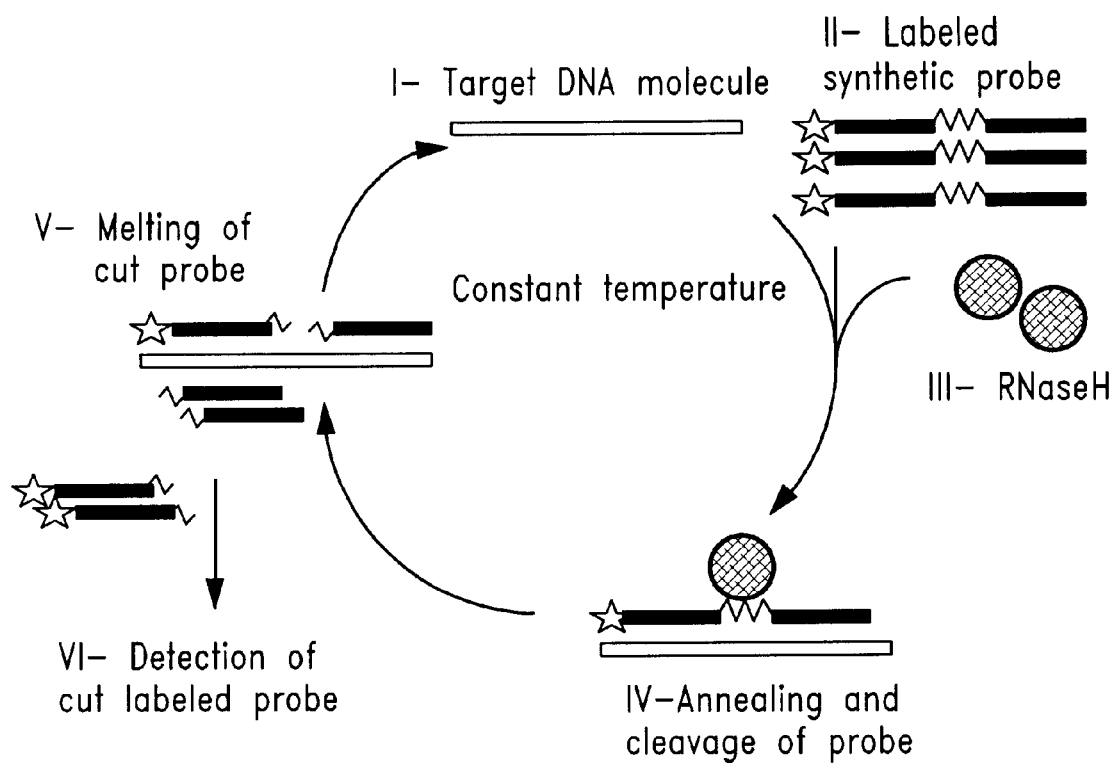
FIG. 1 is a schematic illustration of one representative embodiment of a cycling probe reaction.

Prior to setting forth the invention, it may be helpful to an understanding thereof to first set forth definitions of certain terms that will be used hereinafter.

"Sample or Biological material" refers to a representative portion of a larger whole that is provided for determining the presence or absence of a target nucleic acid molecule. The sample may biological (e.g., culture or clinical samples, crude cellular or microbial lysates, blood, urine or stool), experimentally produced, industrial (e.g., agricultural crops and dairy, waste treatment, food processing, purified extracts), or environmental.

"Nucleic acid molecule" refers to a polymeric nucleotide or polynucleotide, which can have a natural or synthetic origin. Representative examples of nucleic acid molecules include DNA (ds- or ss-DNA), RNA, DNA-RNA hybrids, or nucleic acid molecules which are composed of or contain a nucleic acid analogue (e.g., α-enantiomeric forms of naturally-occurring nucleotides). Furthermore, nucleotides may be modified in their sugar moieties, or in the pyrimidine or purine base moieties. Examples of modification to sugar moieties include modification or replacement of, for example, one or more hydroxyl groups with another group. Modifications to base moieties include alkyl or acylated pyrimidines and purines. In addition, nucleic acid monomers can be linked by phosphodiester bonds, or analogs of such linkages (e.g., phosphorothioate, phosphorodithioate, phosphoramidite, and the like.

"Isolated nucleic acid molecule" refers to a nucleic acid molecule that is not integrated into the genomic DNA of an organism. Isolated nucleic acid molecules include, for example, probes and other synthetically or recombinantly generated nucleic acid molecules.

"Scissile linkage" refers to a nucleic acid molecule which is capable of being cleaved or disrupted without cleaving or disrupting any nucleic acid sequence of the molecule itself or of the target nucleic acid sequence. Scissile linkages include any connecting chemical structure which joins two nucleic acid sequences and which is capable of being selectively cleaved without cleavage of the nucleic acid sequences to which it is joined. The scissile linkage may be a single bond or a multiple unit sequence. An example of such a chemical structure is an RNA sequence. Other chemical structures suitable as a scissile linkage are a DNA sequence, an amino acid sequence, an abasic nucleotide sequence or an abasic nucleotide, or any carbohydrate polymer, i.e., cellulose or starch. When the scissile linkage is a nucleic acid sequence, it differs from the nucleic acid sequences of $NA_1$ and $NA_2$ (described below).

"Probe Containing a Scissile Linkage" refers to a synthetic nucleic acid molecule which is constructed in view of a known sequence to be complementary or substantially complementary to a target nucleic molecule. Within certain embodiments, the probe comprises the structure $[NA_1\text{--}S\text{--}NA_2]_n$ wherein $NA_1$ and $NA_2$ are different, non-complementary nucleic acid molecules and S is a scissile linkage, and n is an integer from 1 to 10.

"Ribonuclease H" ("RNase H") refers to an enzyme capable of specifically cleaving the RNA strand in RNA:DNA hybrid duplex (see generally Crouch & Dirksen in Nucleases, Linn & Roberts (Eds.), pp. 211–241, Cold Spring Harbour Laboratory Press, Plainview, N.Y., 1982).

"Spermine" refers to a polyamine with four positive charges.

"Ribosomal Proteins" refers to protein components of ribosomes of prokaryotic or eukaryotic origin.

The present invention provides means of decreasing background caused by heterologous nucleic acid molecules in samples containing nucleic acid molecules of interest to be detected by a hybridization reaction. For example, within one aspect of the present invention methods are provided for detecting a target nucleic acid molecule comprising the steps of (a) reacting a mixture comprising (i) a target nucleic acid molecule; (ii) a single-stranded nucleic acid probe containing a scissile linkage; (iii) an enzyme capable of cleaving the probe portion of a double-stranded target-probe complex at the scissile linkage; and (iv) ribosomal protein, and/or spermine and/or a detergent and a chelator, under conditions and for a time sufficient to allow the target nucleic acid and probe to hybridize to each other and form a double-stranded target-probe complex, followed by cleavage of the probe and cycling of the target to a new uncleaved probe, such that one or more portions of the cleaved nucleic acid probe are released from said target-probe complex; and (b) determining whether cleaved portions of the nucleic acid probe are produced, and thereby detecting the presence of said target nucleic acid. This, as well as other similar detection/hybridization reactions is discussed in more detail below.

A. Selection and Preparation of the Target Nucleic Acid Molecules

The method of the present invention is suitable for detecting target nucleic acid molecules obtained from viruses, prokaryotes or eukaryotes, or experimentally produced from natural sources, produced by recombinant technology, or chemically synthesized. Representative examples of target nucleic acid molecules include nucleic acid molecules obtained from mammalian cells (e.g., human, macaque, horse, cow, sheep, pig, dog, cat, rat or mouse cells), fungal cells, bacterial cells, plants, viruses and bacteriophage. Methods for selecting target nucleic acid molecules, as well as methods for generating target nucleic acid molecules may be readily accomplished by one of ordinary skill in the art given the disclosure provided herein (see generally, Sambrook et al., *Molecular Cloning: A Laboratory Manual* (2d ed.), Cold Spring Harbor Laboratory Press, 1989).

Single stranded nucleic acid molecules may be obtained and/or prepared directly from a target cell or organism utilizing standard techniques (see, e.g., Sambrook et al., "Molecular Cloning: A Laboratory Manual", Cold Spring Harbor, 1989), or prepared utilizing any of a wide variety of a techniques, including for example, PCR, NASBA, reverse transcription of RNA, SDA, branched-chain DNA and the like.

B. Selection and Synthesis of Probes

The sequence of a probe is based on the target nucleic acid and selected on the basis of several criteria. Briefly, the probe should be able to hybridize with the target sequence and not to any other heterologous nucleic acid sequence that may be present in the sample. There should be minimal or no inter- and intra-probe pairing, i.e., stable hairpins, or stable dimers involving the ribonucleotides. Probe length, non-scissile linkages and scissile linkages are discussed in detail in U.S. Pat. Nos. 4,876,187; 5,011,769; and 5,403,711. The final criteria is testing the probe in CPT reaction against target or heterologous nucleic acids.

As noted above, within one aspect of the present invention the target nucleic acid molecule is reacted with a complementary single-stranded nucleic acid probe having a scissile linkage. Briefly, a wide variety of nucleic acid probes having scissile linkages may be utilized within the context of the present invention. Preferably, the probe is designed such that, upon cleavage by an enzyme which is capable of specifically cleaving the probe-target complex at the scissile link, probe portions are released which are detectable (see U.S. Pat. Nos. 4,876,187, 5,011,769 and 5,403,711). Preferred probe molecules of the present invention generally have the structure $[(NA_1)_x(\text{-S-})_z(\text{-}NA_2)_y]_n$ wherein $NA_1$ and $NA_2$ are molecules composed of nucleic acids or nucleic acid analogues, -S- is a scissile linkage and x, y, and z are integers from 1–100 and n is an integer from 1–10. Within certain particularly preferred embodiments of the invention, $NA_1$ and $NA_2$ may range from 3 to 40 nucleotides, and when S is composed of nucleic acids, may range in size from 2 to 20 nucleotides. In addition, it should be understood that as utilized within the context of the present invention, each of x, y and z can vary with each iteration of n. Although within various embodiments of the invention a single-stranded probe is utilized to react or hybridize to a single-stranded target sequence, the above-described methods should not be limited to only situations wherein complementary probe and target sequences pair to form a duplex.

Within one embodiment, $NA_1$ and $NA_2$ as described above are DNA molecules which may or may not have the same sequence. Alternatively, $NA_1$ and $NA_2$ may be constructed of RNA molecules, which may or may not have the same sequence, or a combination of RNA and DNA molecules. The DNA or RNA molecules utilized may be derived from naturally occurring sources, or they may be synthetically formed. Each of $NA_1$ and $NA_2$ may be from about 5 bases to 10,000 bases in length.

Within other embodiments, $NA_1$ or $NA_2$ may be composed of nucleic acid analogues such as methyl phosphonates, carbamates, amidates, triesters, or "Peptide Nucleic Acids" ("PNA"). For example, PNA oligomers can hybridize to complementary target oligonucleotides (DNA or RNA) sequences with very high specificity. Such duplexes are more stable than the corresponding DNA—DNA or DNA-RNA duplexes (Egholm et al., *Nature* 365:556–568, 1993). Furthermore, PNA can bind to double stranded (ds) DNA by strand displacement (Nielsen et al., *Science* 254:1497–1500, 1991) and hence may obviate the traditional double strand denaturation requirement in sample preparation. Low concentration salt is generally preferred for binding of PNA to dsDNA ($\leq 50$ mM/L of $Na^+$). Moderate concentration of salt can inhibit binding through double strand displacement of PNA to dsDNA. However, once bound the PNA/DNA duplexes are stable to high concentration of salt. Further, these duplexes are also thermally stable compared to oligonucleotide/oligonucleotide duplexes (duplexes of PNA/DNA are more stable by approximately 1° C. per base pair compared to corresponding DNA/DNA). Based on the requirement of high sequence specificity to the target oligonucleotide, greater thermal stability and resistance to high salt concentration of the duplex once formed, PNAs are often ideal molecules for use in the methods described herein. Within certain embodiments, two short PNAs may be linked with scissile linkage and used as a highly sequence specific probe.

Probes of the present invention may also have one or more detectable markers attached to one or both ends (e.g., $NA_1$ or $NA_2$). The marker may be virtually any molecule or reagent which is capable of being detected, representative examples of which include radioisotopes or radiolabeled molecules, fluorescent molecules, fluorescent antibodies, enzymes, or chemiluminescent catalysts.

As noted above, the nucleic acid probe has a scissile linkage which is capable of being cleaved or disrupted without cleaving or disrupting any nucleic acid sequence of the molecule itself, or of the target nucleic acid sequence. As used within the context of the present invention, a scissile linkage is any connecting chemical structure which joins two nucleic acid sequences, and which is capable of being selectively cleaved without cleavage of the nucleic acid sequences to which it is joined. The scissile linkage may be a single bond or a multiple unit sequence. An example of such a chemical structure is an RNA molecule. Other chemical structures which may be suitable as a scissile linkage are DNA molecules, an amino acid sequence, an abasic nucleotide molecule or any carbohydrate polymer (e.g., cellulose or starch). When the scissile linkage is a nucleic acid molecule, it should differ from the nucleic acid sequence of $NA_1$ and $NA_2$.

In the nucleic acid probes described above, when n is greater than one, the unit $NA_1$-S-$NA_2$ repeats. As should be readily understood by one of ordinary skill in the art given the disclosure provided herein, the unit may be the same within each repeat, or may vary randomly in a defined pattern. In addition, the scissile linkage may also vary from unit to unit. For example, one scissile linkage may be an amino acid sequence, and another an RNA molecule.

As noted above, the probes of the present invention may also be linked to a solid support either directly, or through a chemical linker. Representative examples of solid supports include silicaceous, cellulosic, polymer-based, or plastic materials.

Within a particularly preferred embodiment of the invention, nucleic acid probes have the structure: [$NA_1$-S-$NA_2$]$_n$ wherein $NA_1$ and $NA_2$ are nucleic acid sequences, S is a scissile nucleic acid linkage, and n is an integer from 1 to 10. Within this embodiment, $NA_1$ and $NA_2$ are different nucleic acid sequences which are noncomplementary to each other, and -S- is a scissile linkage which is capable of being cleaved or disrupted without cleaving or disrupting $NA_1$ or $NA_2$, or a target nucleic acid sequence capable of hybridizing to the $NA_1$ or $NA_2$ sequences, wherein if the scissile linkage is a nucleic acid sequence it is RNA when both $NA_1$ and $NA_2$ are DNA sequences, or the scissile linkage is DNA when both $NA_1$ and $NA_2$ are RNA sequences. Within certain embodiments of the invention, the probe may contain one or more labels such as a fluorescent or enzymatic label (e.g., quenched fluorescent pairs, or, a fluorescent label and an enzyme label), or a label and a binding molecule such as biotin (e.g., the probe, either in its cleaved or uncleaved state, may be covalently or non-covalently bound to both a label and a binding molecule (see also, e.g., U.S. Pat. No. 5,731,146).

Nucleic acid molecules useful in the methods of the present invention can be constructed on a solid support medium (such as silica gel or controlled pore glass) using either a hydrolysable linkage or a permanent (non-hydrolysable) linkage. Published chemical methods were used for this synthesis. Oligonucleotide molecules are constructed as generally described by Matteucci and Caruthers, *J. Am. Chem. Soc.* 103:3185, 1981; Beaucage and Caruthers, *Tetrahedron Lett.* 22:1859, 1981; Alvarado-Urbina et al., "Automated Synthesis of Gene Fragments," *Science* 214:270–274, 1981; see also U.S. Pat. Nos. 4,876,187, 5,011,769 and 5,403,711. For oligonucleotide analogs and conjugates synthesis see generally Agrawal (ed.) *Protocols For Oligonucleotides And Analogs, Synthesis; Synthesis and Properties,* Methods in Molecular Biology Volume 20, Humana Press Inc., 1993; Egholm et al., *Nature* 365:566–568, 1993; Dueholm et al., *J. Org. Chem.* 59:5767–5773, 1994; Agrawal (ed.) *Protocols For Oligonucleotide Conjugate, Synthesis And Analytical Techniques,* Methods in Molecular Biology Volume 26, Humana Press Inc., 1994. For non-isotopic probes see generally Kriscka, *Non-Isotopic DNA Probe Techniques,* Academic Press Inc., New York, 1992.

Briefly, oligonucleotide synthesis is accomplished in cycles wherein each cycle extends the oligonucleotide by one nucleotide. Each cycle consists of four steps: (1) deprotecting the 5'-terminus of the nucleotide or oligonucleotide on the solid support; (2) coupling the next nucleoside phosphoroamidite to the solid phase immobilized nucleotide; (3) capping the small percentage of the 5'-OH groups of the immobilized nucleotides which did not couple to the added phosphoramidite; and (4) oxidizing the oligonucleotide linkage to a phosphotriester linkage.

Representative methods for synthesizing oligonucleotides and biotinylation and fluoresceination of the oligonucleotides are shown in Example 1.

C. Ribonuclease H

Ribonuclease H (RNase H) occurs in organisms ranging from prokaryotes to eukaryotes (reviewed by Crouch & Dirksen in Nucleases, Linn & Roberts (Eds.), pp. 211–241, Cold Spring Harbour Laboratory Press, Plainview, N.Y., 1982). RNase H can be obtained commercially, or prepared according to known techniques. In particular, RNase H can be isolated and purified from thermophilic and non-thermophilic organisms (see for example Kanaya et al., *J. Bio. Chem.* 258:1276–1281, 1983; Kanaya & Itaya, *J. Biol. Chem.* 267:10184–10192, 1992). RNase H useful for this invention can be obtained from thermophilic bacteria such as *Thermus thermophilus* or alternatively, the RNase H gene can be cloned and expressed in *E. coli* by the method of Kanaya & Itaya, supra. Recombinant technologies can also be used for thermostablizing RNase H variants from non-thermostable organisms (Ishikiwa et al., *Protein Eng.* 6:85–91, 1993).

Non-thermostable RNase H useful in this invention can be isolated and purified from *E. coli* by the method of Kanaya et al., supra. *T. thermophilus* and *E. coil* RNase H are also available commercially. *T. thermophilus* RNase H has greater residual activity at 65° C. (Itaya & Kondo, *Nucl. Acids Res.* 16:4443–4449, 1991) and has 34° C. higher thermal unfolding temperature than the *E. coli* enzyme (Ishikawa et al., *J. Mol. Biol.* 230:529–542, 1993). RNase H requires divalent cations for its catalytic activity (Crouch and Dirksen, supra).

D. Accessory Proteins and Ribosomal Proteins

Upon purification of proteins that occur during recombinant production of RNase H, it was serendipitously discovered that other proteins were being co-purified as part of RNase H preparation that caused variation in the CPT reactions containing heterologous DNA. Preparations of several RNase H batches produced with slight variations in the column fraction collected around the main RNase H peak did not adversely effect CPT reactions when used in simple systems, i.e., where only the target and the probe was present. However, these same batches were found to consistently differ from each other in activity when used in complex CPT reactions that contained heterologous DNA. This is demonstrated in Example 3 and Table 1. It was also discovered that not only were co-purified proteins present, but that the relative quantities of these proteins affected the CPT reaction. This is demonstrated in Example 4, FIG. 2 and Table 2. Another surprising aspect of this discovery was that highly purified RNase H (>95%) did not perform as well in cycling reactions that contained heterologous DNA. Since it was shown that the CPT reaction could be improved with an increase of these co-purified proteins with purified RNase H, these proteins were referred to as accessory proteins. By SDS gel electrophoresis the two main accessory proteins were found to have approximately 10 kDa and 13 kDa putative molecular masses and were referred to as the "10 kDa" and "13 kDa" accessory proteins, respectively. The accessory proteins were purified and tested in CPT with partially-purified and purified RNase H. It was proven that these accessory proteins contributed to the improvement of CPT when using purified RNase H as shown in Example 6. Upon further characterization of the proteins by amino acid sequencing, it was revealed unexpectedly that these proteins had similar amino acid sequences to the L34 and S19 ribosomal proteins of *E. coli*.

Ribosomal proteins are found in both prokaryotic and eukaryotic organisms and are involved in translation of the genetic message to polypeptide chains. The *E. coli* 70 S ribosome has two subunits called 30 S and 50 S. The 30 S subunit is composed of 21 different proteins and 16 S rRNA, and the 50 S subunit is composed of 32 different proteins and a single strand each of 5 S and 23 S rRNA. It has been observed that the molecular mass of ribosomal proteins obtained by the sedimentation equilibrium and SDS-gel electrophoresis were consistently higher than those obtained by chemical means from the primary amino acid sequences. The former techniques affects the smaller and very basic proteins much more than larger or less basic ones. Ribosomal proteins are relatively insoluble in aqueous solutions and have great propensity to aggregate (Giri et al., supra). Wittmann-Liebold and co-workers, cited in Giri et al., supra, have determined the primary structure of all *E. coli* ribosomal proteins. The majority of the ribosomal proteins are relatively basic and have high isoelectric points (Kaltschimdt, cited in Giri et al., supra), with a high content of basic amino acids. The molecular mass of L34 is 5.4 kDa and has 46 amino acid residues, and S19 is 10.3 kDa and has 91 residues (Wittmann-Liebold, cited in Giri et al., supra, Wittmann, cited in Giri et al., supra).

As described in more detail below, both purified and synthetic L34 ribosomal proteins were tested in CPT reactions. Surprisingly, both the synthetic L34 and a crude extract of ribosomal proteins from the eukaryote yeast improved CPT reaction when only purified RNase H was utilized. Preparation of *E. coli* ribosomal proteins are well known in the art see generally Giri et al. supra. Yeast ribosomal proteins can be prepared generally by the methods of Katschimdt & Wittman, *Anal Biochem* 36:401–412, 1970, Raue et al., *Methods Enzymol.* 194:453–477, 1991.

E. Spermine

As noted above, it has also unexpectedly been discovered that when running a cycling probe reaction, spermine, or a combination of spermine and ethylenebis(oxyethylenitrilo)-tetraacetic acid (EGTA), in samples containing a concentration of heterologous DNA decreased the background, but, maintained the signal to noise ratio. The most significant improvement in signal to noise ratio occurred with the combination of spermine and EGTA. In contrast, when only low concentrations of heterologous DNA are present, spermine decreased background, but also decreased the signal to noise ratio. Therefore, utilization of the polyamine spermine by itself or in combination with chelators, EGTA and also EDTA, reduces background caused by heterologous DNA in samples used for detection of target nucleic acid by CPT. This invention applies to detection of both synthetic and natural nucleic acid targets. Further spermine has also been found to improve CPT reactions using solid support.

F. Methods and Assay Conditions

As noted above, the present invention provides methods for detecting target nucleic acid molecules utilizing a hybridization reaction. For example, within one aspect of the present invention methods are provided for detecting a target nucleic acid molecule comprising the steps of (a) reacting a mixture comprising (i) a target nucleic acid molecule; (ii) a single-stranded nucleic acid probe containing a scissile linkage; (iii) an enzyme capable of cleaving the probe portion of a double-stranded target-probe complex at the scissile linkage; and (iv) ribosomal protein and/or spermine, and/or a detergent and a chelator, under conditions and for a time sufficient to allow the target nucleic acid and probe to hybridize to each other and form a double-stranded target-probe complex, followed by cleavage of the probe and cycling of the target to a new uncleaved probe, such that one or more portions of the cleaved nucleic acid probe are released from said target-probe complex; and (b) detecting cleaved portions of the nucleic acid probe, thereby determining the presence of said target nucleic acid. Representative examples of suitable assays and methods are described in more detail within U.S. Pat. Nos. 5,011,769 and 5,403,711. Other variations of such assays include 'exponential' cycling reactions such as described in U.S. Pat. No. 5,403,711 (see also U.S. Pat. No. 5,747,255).

The compositions provided herein (e.g., reaction mixtures comprising a probe, primer or other oligonucleotide, a target or template, and ribosomal protein and/or spermine and/or a detergent and chelator) may be utilized in a wide variety of other/related hybridization methods (e.g., U.S. Pat. Nos. 5,210,015; 5,487,972; 5,422,253; 5,691,142; 5,719,028;

5,130,238; 5,409,818; 5,554,517; 5,589,332, 5,399,491; 5,480,784; 5,215,899; 5,169,766; 5,194,370; 5,474,916; 5,698,400; 5,656,430; and PCT publication Nos. WO 88/10215; WO 92/08800, WO 96/02668; WO 97/19193; WO 97/09444; WO 96/21144; WO 92/22671). For example, in another aspect of the present invention, methods are provided for detecting a target nucleic acid molecule comprising the steps of (a) reacting a mixture comprising (i) a target nucleic acid molecule; (ii) one or more single-stranded oligonucleotide molecule(s); (iii) an enzyme capable of cleaving one of the oligonucleotide molecules that forms one or more double-stranded target-oligonucleotide complex(es); and (iv) ribosomal protein and/or spermine, and/or a chelator and a detergent, under conditions and for a time sufficient to allow the target nucleic acid and oligonucleotide molecule(s) to hybridize to each other and form double-stranded target-oligonucleotide complex(s), followed by cleavage of one of the target-oligonucleotide complexes, and (b) determining whether cleaved portions of the nucleic acid probe are produced, and thereby detecting the presence of target nucleic acid.

In a second aspect of the present invention, methods are provided for detecting a target nucleic acid molecule comprising the steps of (a) reacting a mixture comprising (i) a target nucleic acid molecule; (ii) one or more single-stranded oligonucleotide molecule(s); (iii) an enzyme capable of cleaving one of the oligonucleotide molecules that forms one or more double-stranded target-oligonucleotide complex(es); and (iv) ribosomal protein, and/or spermine, and/or a chelator and a detergent, under conditions and for a time sufficient to allow the target nucleic acid and oligonucleotide molecule(s) to hybridize to each other and form double-stranded target-oligonucleotide complex(s), followed by cleavage of one of the oligonucleotide complexes and cycling of the target to a new oligonucleotide molecule(s), such that one or more portions of the cleaved oligonucleotide molecules are released from the target-oligonucleotide complex; and (b) determining whether cleaved portions of the nucleic acid probe are produced, and thereby detecting the presence of the target nucleic acid.

In a third aspect of the present invention, methods are provided for detecting a target nucleic acid molecule comprising the steps of (a) reacting a mixture comprising (i) a target nucleic acid molecule; (ii) one or more single-stranded oligonucleotide molecule(s); (iii) an enzyme capable of cleaving one of the oligonucleotide molecules that forms one or more double-stranded target-oligonucleotide complex(es); and (iv) ribosomal protein, and/or spermine, and/or a chelator and a detergent, under conditions and for a time sufficient to allow the target nucleic acid and oligonucleotide molecule(s) to hybridize to each other and form double-stranded target-oligonucleotide complex(s); followed by a primer extension of one of the oligonucleotides, and then enzymatic cleavage of one of the oligonucleotide complexes and cycling of the target to a new oligonucleotide molecule(s), such that one or more portions of the cleaved oligonucleotide molecules are released from the target-oligonucleotide complex; and (b) determining whether cleaved portions of the nucleic acid probe are produced, and thereby detecting the presence of the target nucleic acid.

Other related methods include for example, those described in U.S. Pat. Nos. 5,422,253, 5,691,142, 5,130,238, 5,589,332, 5,399,941, 5,270,184. More specifically, methods for cleaving a target nucleic acid at a specific target site in the presence of heterologous nucleic acid molecules are provided, comprising the general steps of (a) selecting a target site on a target nucleic acid, (b) creating a pilot nucleic acid with a sequence complementary to the sequence of a first region of the target nucleic acid, (c) reacting a mixture comprising (i) a target nucleic acid molecule; (ii) pilot nucleic acid; (iii) an enzyme capable of cleaving the target molecule in a double-stranded target-pilot complex; and (iv) ribosomal protein, and/or spermine, and/or a chelator and a detergent, (d) forming a cleavage structure comprising the target nucleic acid and the pilot nucleic acid, wherein the pilot nucleic acid does not contain any region that is not annealed to the target nucleic acid, wherein the first region of the target nucleic acid is annealed to the pilot nucleic acid to form a duplex and wherein a second region of the target nucleic acid contiguous to the duplex is not annealed to the pilot nucleic acid, forming a junction site between the duplex region and the non-annealed region, and (e) exposing the cleavage structure to a cleavage agent which cleaves the cleavage structure at a specific target site within the first region of the target nucleic acid which is annealed to the pilot nucleic acid to form a duplex, within two nucleotides of the junction site, in a manner independent of the sequence of the cleavage structure, wherein the cleavage agent is selected from the group consisting of a 5' nuclease activity of a DNA polymerase and the gene 6 product from bacteriophage T7, and (f) incubating the cleavage structure and cleavage agent wherein cleavage occurs.

Within other related aspects, methods are provided for detecting the presence of a specific target DNA molecule in the presence of heterologous nucleic acid molecules comprising the general steps of a) providing: i) a target nucleic acid having a first and a second portion; ii) a first oligonucleotide complementary to the first portion of the target nucleic acid, and iii) a second oligonucleotide having a 5' and a 3' end and a region which is complementary to the second portion of the target nucleic acid, the non-complementary region of the second oligonucleotide providing a single-stranded arm at its 5' end; (iv) ribosomal protein, and/or spermine, and/or a chelator and a detergent; and b) mixing the target nucleic acid, the first oligonucleotide, the second oligonucleotide and (iv) ribosomal protein and/or spermine, under conditions wherein the first oligonucleotide and the 3' end of the second oligonucleotide are annealed to the target DNA sequence so as to create a first cleavage structure having a single-stranded arm, c) providing a cleavage means under conditions such that cleavage of the first cleavage structure occurs at a site located within the second oligonucleotide in a manner dependent upon the annealing of the first and second oligonucleotides on the target nucleic acid, thereby liberating the single-stranded arm of the cleavage structure generating a third oligonucleotide, d) providing a first hairpin structure having a single-stranded 3' arm, a single-stranded 5' arm and ribosomal protein and/or spermine, under conditions wherein the third oligonucleotide anneals to the single-stranded 3' arm of the first hairpin thereby creating a second cleavage structure having a single-stranded 5' arm, e) providing conditions under which cleavage of the second cleavage structure occurs by the cleavage means liberating the single-stranded 5' arm of the second cleavage structure so as to create reaction products comprising a fourth oligonucleotide and a first cleaved hairpin detection molecule, f) providing a second hairpin structure having a single-stranded 3' arm, a single-stranded 5' arm and ribosomal protein and/or spermine, under conditions wherein the fourth oligonucleotide anneals to the single-stranded 3' arm of the second hairpin thereby creating a third cleavage structure having a single-stranded 5' arm, g) providing conditions under which cleavage of the third cleavage structure occurs by the cleavage means liberating the single-stranded 5' arm of the third cleavage structure so as to create reaction products comprising generating a fifth oligonucleotide identical in sequence to the third oligonucleotide and a second cleaved hairpin detection molecule, and h) detecting the presence of the first and second cleaved hairpin detection molecules.

Within other aspects, methods are provided for the amplification of a specific nucleic acid sequence in the presence of heterologous nucleic acid molecules, at a relatively constant temperature and without serial addition of reagents, comprising the steps of: (A) providing a single reaction medium containing reagents comprising (i) a first oligonucleotide primer, (ii) a second oligonucleotide primer comprising an antisense sequence of a promoter, (iii) a DNA-directed RNA polymerase that recognizes the promoter, (iv) an RNA-directed DNA polymerase, (v) a DNA-directed DNA polymerase, (vi) a ribonuclease that hydrolyzes RNA of an RNA-DNA hybrid without hydrolyzing single- or double-stranded RNA or DNA, (vii) ribonucleoside and deoxyribonucleoside triphosphates, (viii) dimethylsulfoxide and (ix) ribosomal protein, and/or spermine, and/or a chelator and a detergent; and then (B) providing in the reaction medium RNA comprising an RNA first template which comprises the specific nucleic acid sequence or a sequence complementary to the specific nucleic acid sequence, under conditions such that a cycle ensues wherein (i) the first oligonucleotide primer hybridizes to the RNA first template, (ii) the RNA-directed DNA polymerase uses the RNA first template to synthesize a DNA second template by extension of the first oligonucleotide primer and thereby forms an RNA-DNA hybrid intermediate, (iii) the ribonuclease hydrolyzes RNA which comprises the RNA-DNA hybrid intermediate, (iv) the second oligonucleotide primer hybridizes to the DNA second template, (v) the DNA-directed DNA polymerase uses the second oligonucleotide primer as template to synthesize the promoter by extension of the DNA second template; and (vi) the DNA-directed RNA polymerase recognizes the promoter and transcribes the DNA second template, thereby providing copies of the RNA first template; and thereafter (C) maintaining the conditions for a time sufficient to achieve a desired amplification of the specific nucleic acid sequence.

Within other aspects, methods are provided for detecting a target nucleic acid molecule, in the presence of heterologous nucleic acid molecules, in a solution, comprising the general steps of providing in the solution ribosomal protein, and/or spermine, and/or a chelator and a detergent and under conditions wherein two complementary nucleotide molecules will hybridize, a ribozyme molecule, a labelled co-target nucleic acid molecule and the target nucleic acid molecule, wherein the co-target and the target molecules have different sequences and wherein the ribozyme molecule comprises two regions complementary to portions of the co-target and target nucleic acid molecules, wherein the first portion is present on the labelled co-target nucleic acid molecule which contains a cleavage site for the ribozyme and the second portion is present on the target nucleic acid molecule, wherein the complementary regions include at least the minimum number of complementary nucleotides to obtain hybridization between the ribozyme molecule and the co-target and target nucleic acid molecules, allowing the ribozyme molecule to react with the labelled co-target nucleic acid molecule and the target nucleic acid molecule, and detecting the presence of free label when the target nucleic acid molecule is present in solution as compared with when the target nucleic acid molecule is not present in solution.

Within yet other aspects, methods are provided for synthesizing multiple copies of a target nucleic acid sequence, in the presence of heterologous nucleic acid molecules, comprising the general steps of (a) treating a nucleic acid which comprises an RNA target sequence with a first oligonucleotide which comprises a first primer which has a hybridizing sequence sufficiently complementary to a 3'-terminal portion of the target sequence to hybridize there with and which optionally has a sequence 5' to the hybridizing sequence which includes a promoter for an RNA polymerase, ribosomal protein, and/or spermine, and/or a chelator and a detergent and, under conditions whereby an oligonucleotide/target sequence hybrid is formed and DNA synthesis may be initiated, (b) extending the primer in an extension reaction using the target as a template to give a DNA primer extension product complementary to the RNA target; (c) separating the DNA primer extension product from the RNA target using an enzyme which selectively degrades the RNA target; (d) treating the DNA primer extension product with a second oligonucleotide which comprises a primer or a splice template and which has a hybridizing sequence sufficiently complementary to the 3'-terminal portion of the target sequence to hybridize therewith, under conditions whereby an oligonucleotide/target sequence hybrid is formed and DNA synthesis may be initiated, provided that if the first oligonucleotide does not have a promoter, then the second oligonucleotide is a splice template which has a sequence 5' to the hybridizing sequence which includes a promoter for an RNA polymerase; (e) extending the 3'-terminus of either the second oligonucleotide or the first primer extension product, or both, in a DNA extension reaction to produce a template for an RNA polymerase; and (f) using the template of step (e) to produce multiple RNA copies of the target sequence using an RNA polymerase which recognizes the promoter sequence; wherein the method is conducted under conditions of constant temperature and wherein a reverse transcriptase comprising RNase H activity is used in the method, and no other enzyme comprising RNase H activity is used in the method.

Within other aspects, methods are provided for generating an amplifying a nucleic acid fragment comprising the general steps of (a) specifically hybridizing a first primer 5' to a target nucleic acid sequence, the first primer containing a restriction enzyme recognition sequence 5' to a target binding region, (b) simultaneously with (a), hybridizing a second primer 5' to the first primer, under conditions which include ribosomal protein, and/or spermine, and/or a chelator and a detergent, (c) extending the first and second primer so that the first primer extension product is displaced from the target nucleic acid sequence by extension of the second primer, (d) making the first primer extension product double stranded by synthesizing a complementary strand, and (e) amplifying the first primer extension product in an amplification reaction in which the restriction enzyme recognition site of the double stranded nucleic acid fragment is nicked by a restriction enzyme.

Representative examples of further suitable assay formats including any of the above assays which are carried out on solid supports such as dipsticks, magnetic beads, and the like (see generally U.S. Pat. Nos. 5,639,428; 5,635,362; 5,578, 270; 5,547,861; 5,514,785; 5,457,027; 5,399,500; 5,369, 036; 5,260,025; 5,208,143; 5,204,061; 5,188,937; 5,166, 054; 5,139,934; 5,135,847; 5,093,231; 5,073,340; 4,962, 024; 4,920,046; 4,904,583; 4,874,710; 4,865,997; 4,861,728; 4,855,240; and 4,847,194).

G. Detection

After cycling (or performing the detection reaction), the presence or absence of a cleaved nucleic acid probe (or other reaction product) can be detected with direct or indirect formats using various ligands, labels or tags that are well known in the art. Briefly, detection can be carried out with or without direct labeling of oligonucleotides and with or without a separation step for removing non-hybridized nucleic acid molecules.

Unlabeled nucleic acid probes (or other products of the detection reaction) can be detected by the physical changes that occur when single strand molecules form duplexes. The change in state can be detected by use of dsDNA intercalators (dyes) or antibodies. Examples of intercalators include ethidium bromide, YO-PRO-1 and SYBR Green I (cited in Ririe et al., Anal. Biochem. 245:154–160, 1997). Alternatively, hyperchromic and ultra violet spectrophotometric methods can be used. Another means is by detecting a change in the electrical conductivity when duplexes are formed.

Alternatively, the nucleic acid probe can be labeled directly prior to cycling (or detection reaction), or, indirectly with the use of a tag (e.g., avidin or biotin) prior to cycling and then attaching a label to the tag after cycling. The labels can be, for example, radioisotopic, enzymatic, fluorescent, chemiluminiscent, or bioluminescent (see generally Keller and Manak, supra, Wetmur, supra). For use in solution or immobilized assays, the label can be attached directly or indirectly to the nucleic acid probe. In yet further embodiments, reaction products may be detected utilizing solid supports as discussed above, and/or through further processing (e.g., by use of extension reactions and the like).

The following examples are offered by way of illustration, and not by way of limitation.

EXAMPLES

Example 1
Construction of Nucleic Acid Probes

Nucleic acid molecules can be synthesized utilizing standard chemistries on automated, solid-phase synthesizers such as PerSeptive Biosystems Expedite DNA synthesizer (Boston, Mass.), PE Applied Biosystems, Inc.'s Model 391 DNA Synthesizer (PCR-MATE EP) or PE Applied Biosystems, Inc.'s Model 394 DNA/RNA Synthesizer (Foster City, Calif.). Preferably, PerSeptive Biosystems Expedite DNA synthesizer is used and the manufacturer's modified protocol for making oligonucleotides is carried out.

Reagents for synthesis of oligonucleotides are commercially available from a variety of sources including synthesizer manufacturers such as PerSeptive Biosystems, PE Applied Biosystems Inc., Glen Research (Sterling, Va.) and Biogenex. For DNA and RNA synthesis, the preferred fluorescein amidite, phosphoramidites of deoxy-and ribonucleosides, 2'-O-methyl and reagents, such as activator, Cap A, Cap B, oxidizer, and trityl deblocking reagent are available from PerSeptive Biosystems. Biotin-TEG-phosphoroamidite and Biotin-TEG-CPG are available from Glen Research. Ammonium hydroxide (28%) used for the deprotection of oligonucleotides is purchased from Aldrich. 1 M Tetrabutylammonium fluoride (TBAF) used for removing the 2'-O-tert-butyldimethylsilyl group is purchased from Aldrich and used after drying over molecular sieves for 24 hours. All buffers are prepared from autoclaved water and filtered through 0.2 μm filter.

The following procedure is used for preparing biotinylated and/or fluoresceinated oligonucleotides. Biotin-TEG-CPG (1 μmol) is packed into a synthesis column. Nucleoside phosphoramidites are then linked to make the defined nucleic acid sequence using PerSeptive Biosystem's modified protocol for making oligonucleotides. Fluorescein-amidite is dissolved in acetonitrile to a final concentration of 0.1 M. The fluorescein amidite is loaded on the synthesizer and added to the 5'- end of the oligonucleotide. Alternatively, phosphoramidite containing thio-linker is added at the 5'- terminal of the chimeric probe using the modified protocol. After the deprotection step described below, the probe is purified by reverse phase HPLC using Millipore's R-2 resin which retains the trityl containing oligonucleotide. In order to generate free reactive thio-group, the HPLC purified probe is treated with silver nitrate for 90 minutes at room temperature followed by neutralization of silver nitrate with dithiotheritol (DTT). The fluorescein-maleimide is then added to the free thio-group of the probe and then purified either by HPLC or by electrophoresis as described below.

After the synthesis of the oligonucleotide sequence, the resin bound oligonucleotide is treated initially with 25% ethanol-ammonium hydroxide (4 ml) at room temperature for 1 hour and subsequently at 55° C. for 16 hours in a closed tube. The tube is cooled, supernant removed and concentrated to dryness in order to remove ammonia. The residue is dissolved in 1 ml of water and filtered through a 0.2 μm filter.

The $OD_{260}$ is determined and an aliquot of approximately 2 $OD_{260}$ units is injected into the R-2 column of Biocad's HPLC to obtain a base line on the chromatogram for the tert-butyldimethylsilyl groups of the chimeric probe.

The remaining probe solution is lyophilized by centrifugal vacuum evaporator (Labconco) in a 1.5 ml microcentrifuge tube. The resulting oligonucleotide residue is deprotected with 1.0 M TBAF for 24 hours. To determine the extent of desilylation which has taken place, an aliquot of the TBAF reaction mixture is injected into the HPLC (R-2 column) using a linear gradient of 0 to 60% acetonitrile in 50 mM triethylammonium acetate (TEAA), pH 6.5. If only a partial desilylation has occurred, the TBAF reaction mixture is allowed to proceed for an additional 12 to 16 hours for complete removal of the protecting groups. The TBAF reaction mixture is quenched with 100 mM NaOAc, pH 5.5 and evaporated to dryness. The crude oligonucleotide product is desalted on a P-6 column (2 cm×10 cm, Bio-Rad), the fractions are concentrated to approximately 1 ml and the concentration measured at $OD_{260}$.

The crude oligonucleotide is purified by polyacrylamide gel electrophoresis (PAGE) using 20% polyacrylamide-7 M urea. The running gel buffer is 1×TBE (Tris-Borate- ethylenediamine tetraacetic acid (EDTA), pH 8.3 ) and the electrophoresis is carried out at 50 mA current for 3.5 to 4 hours. The oligonucleotide band is visualized with UV light, excised, placed in a 15 ml plastic conical tube and extracted by crushing and soaking the gel in 5 ml of 50 mM NaOAc (pH 5.5) for approximately 12 hours. The tubes are then centrifuged at 3000 RPM and the supernatant carefully removed with a Pasteur pipette. The gel is rinsed with 2 ml of the extraction buffer to remove any residual product. The combined extract is concentrated to a volume of approximately 1 ml and desalted on a P-6 column. The fractions containing the probe are pooled and concentrated to a final volume of approximately 2 ml. The analytical purity of oligonucleotides is checked by labeling the 5'- end of oligonucleotide with $[\gamma^{32}P]$-ATP and T4-polynucleotide kinase and then running the labeled oligonucleotide on PAGE. $OD_{260}$ is measured using Hewlett Packard's 845X UV spectrophotometer. The oligonucleotide solution is filtered through a 0.2 μm filter and stored at −20° C.

Utilizing the above-noted procedure, the following oligonucleotides were synthesized (upper case letters have been utilized to denote deoxyribonucleotides, and lower case letters have been utilized to denote ribonucleotides):

---

ARK2 Probe Sequence (SEQ ID NO:1)
    5'-GTC GTC AGA CCC aaa aCC CCG AGA GGG-3'
ARK2T Target Sequence (SEQ ID NO:2)
    5'-CCC TCT CGG GGT TTT GGG TCT GAC GAC-3'
ARK2-95 Target Sequence (SEQ ID NO:3)
5'-ATA CGA CTC ACT ATA GGG AAT TCG AGC TCG GTA CCC CTC TCG GGG TTT TGG GTC TGA CGA CTG CAG GCA TGC AAG CTT GGC ACT GGC CGT CGT TT-3'
mecA945-29 Probe Sequence (SEQ ID NO:4)
5'-AATAGAGAAAAAGaaaaAAGATGGCAAAG-3'
mecA945-T Target Sequence (SEQ ID NO:5)
5'-CTT TGC CAT CTT TTT TCT TTT TCT CTA TT-3'
mecA834-25 (SEQ ID NO:6)
5'-TGG TAA AAA GGG ACT CGA AAA ACT T-3'
mecAL1039-22 (SEQ ID NO:7)
5'-GGT GGA TAG CAG TAC CTG AGC C-3'

---

Example 2
Cycling Probe Reactions

Cycling probe technology (CPT) reactions are performed under conditions essentially described in WO 95/14106 and Bekkaoui et al., *BioTechniques* 20(2): 240–248, 1996, 6201. The chimeric probe is 5' labeled with radioactive [$^{32}$P]-ATP (Sambrook et al., 1990) using T4 polynucleotide kinase (RTG; Pharmacia Biotech, Piscataway, N.J.). Unless otherwise specified, the labeled probe is purified from non-incorporated [$^{32}$P]-ATP by G50 NICK column (Pharmacia) chromatography. Unless otherwise indicated, the final cycling reaction mixture contains the specified concentrations of chimeric probe and synthetic or natural nucleic acid target in Tris or TES cycling buffer (Tris- or TES-CB) which may have the following: Triton X-100®, $MgCl_2$, 50 mM Tris, pH 8.1 or 20 mM TES buffer, pH 6.8. Sample preparations, probes, targets, buffer compositions, addition of test additives, heterologous DNA, and other components details are described in the following examples.

Unless otherwise specified, the CPT reactions are incubated for 30 minutes at 65° C. and then stopped by addition of urea loading buffer (10 M urea, 100 mM EDTA and 0.025% each of blue bromophenol and xylene cyanol) on ice. The reaction mixtures were then resolved by 7 M urea—20% acrylamide/bisacrylamide (19:1) gel electrophoresis (SDS-PAGE) at 500 Volts, with cooling. The gel was analyzed on a PhosphorImager™ utilizing ImageQuant™ software (Molecular Dynamics, Sunnyvale, Calif.). The amount of cycled probe was estimated by integration of the areas of bands corresponding to intact and cleaved probe.

Unless otherwise stated, in a CPT reaction Percent Probe Cut is the total amount of cut probe relative to the total amount of the input probe (Equation No. 1).

$$\text{Percent Probe Cut}=(\text{Probe Cut/Total input probe})\times 100 \quad (1)$$

In a simple CPT system, the C1 background refers to the Percent Probe Cut in the reaction buffer without RNase H or homologous target present. C2 refers to Percent Probe Cut in the presence of RNase H but without homologous target (Equation No. 2).

$$C2=(\text{Probe cut/Total input probe})\times 100 \quad (2)$$

For complex CPT system, C3 refers to Percent Probe Cut in the sample (biological samples that contains extraneous components, such as heterologous DNA or proteins) in the absence of RNase H. C4 refers to Percent Probe Cut in the biological sample in the presence of RNase H, but in the absence of homologous target (Equation No.3).

$$C4=(\text{Probe cut/Total input probe})\times 100 \quad (3)$$

Net Percent Probe Cut is the percent of probe cut due to homologous target and is calculated by subtracting the background C2 (simple system), or C4 (complex system) from the Percent Cut (Equations No. 4 or 5, respectively).

$$\text{Net Percent Cut}=\text{Percent Cut}-C2 \quad (4)$$

$$\text{Net Percent Cut}=\text{Percent Cut}-C4 \quad (5)$$

Signal to noise ratio (S:N) for CPT is defined as the ratio of the Percent Probe Cut in the presence of the homologous target to the C2 (simple system, Equation No. 6) or C4 (complex system, Equation No. 7).

$$S{:}N=\text{Percent Cut}/C2 \quad (6)$$

$$S{:}N=\text{Percent Cut}/C4 \quad (7)$$

Example 3
Thermostable RNase H Preparations and Variation in CPT Reactions in the Presence of Heterologous DNA This example demonstrates that differences are observed in CPT reactions containing heterologous DNA can be caused by *Thermus thermophilus* RNase H enzyme batch used in the reaction.

Native *T. thermophilus* RNase H was purified as described by Itaya & Kondo, *Nucleic Acids Res.* 19:4443–4449, 1991, Kanaya & Itaya, *J. Biol. Chem.* 267:10184–10192, 1992 and as modified by Bekkaoui et al., *BioTechniques* 20:240–248, 1996. Initially, each of the final RNase H batch preparations were analyzed by separation by SDS PAGE and silver staining of the proteins. These RNase H batches appeared to be pure and were thus considered equivalent. Initial experiments using simple systems (no heterologous DNA) indicated that there was little variation between the batches and thereby confirming their equivalence. However, when several batches were tested in CPT reactions that included heterologous DNA, such as hgDNA, there were large unexplained variations in the results of the CPT reaction. Therefore the following experiment was designed to examine the RNase H batch to batch variation in a systematic manner.

In this experiment six separate batches of thermostable RNase H produced by the above method were compared in CPT reactions in the presence or absence of hgDNA.

The following RNase H batch preparations were compared: A6-1, A7-1, A8-1, A10-1, A11-1 and A12-1. The chimeric probe ARK2 (SEQ ID NO:1) was synthesized and labeled as described in Example 1. The homologous target from *Mycobacterium tuberculosis* and heterologous DNA from *Mycobacterium gordonnae* were prepared as described by Beggs et al., *J. Clin. Microbiol.* 34: 2985–2989, 1996. Each type of DNA was diluted in 1× Tris Cycling Buffer (CB, 8 mM $MgCl_2$, 0.025% Triton X-100® and 50 mM Tris-HCl, pH 8.1). The CPT reaction and analysis was carried out as described in Example 2 with the following exceptions: 3000 cpm of ARK2 probe (SEQ ID NO:1), 2.5 ng of *M. tuberculosis* genomic DNA ($5 \times 10^5$ cell equivalent of DNA), 4 µg RNase H from the specified batch preparation, 1 µg of *E. coli* single stranded binding protein (SSB), with or without 200 ng hgDNA, in Tris cycling buffer in a final reaction volume of 40 µl. The C4 background was obtained as described in Example 2 using non-specific genomic *M. gordonnae* DNA and this value was subtracted from the test values to obtain the Net Percent Probe Cut as described in Example 2.

Table 1 shows the results of detecting *M. tuberculosis* by CPT using different RNase H enzyme batches in the presence or absence of hgDNA. The Net Percent Probe Cut were high and there was a little variation observed between the batches of RNase H used in the CPT reactions in samples with no addition of hgDNA and using the same concentration of RNase H from each batch. However, in the presence of 200 ng of hgDNA, the Net Percent Probe Cut using the different RNase H batch showed two surprising differences. The first difference was that the Net Percent Probe Cut decreased and the second difference was that there was a high variability in the Net Percent Probe Cut between the enzyme batches, ranging from 13% to 50%.

These results are interesting because if the presence of hgDNA caused the decrease in the Net Percent Probe Cut, then there should have been a proportional decrease compared to similar samples which had no hgDNA present. Therefore, these results suggest that the only source of variation besides hgDNA, were the different enzyme batches that were used in the CPT reactions, since the remaining components and conditions were the same in each reaction.

TABLE 1

The effect of different batches of thermostable RNase H on the C4 background and Net Percent Probe Cut in the presence or absence of hgDNA (200 ng) using chimeric probe ARK2 and genomic *M. tuberculosis* DNA target in the presence of *M. gordonnae* and SSB in CPT reactions.

| RNase H Batch Preparation | *M. gordonnae* C4 (%) | Net Probe Cut (%)[1] | *M. gordonnae* & hgDNA C4 (%) | Net Probe Cut (%)[2] |
|---|---|---|---|---|
| A6-1 | 1 | 80 | 6 | 47 |
| A7-1 | 3 | 70 | 9 | 36 |
| A8-1 | 0 | 77 | 8 | 50 |
| A10-1 | 0 | 83 | 6 | 16 |

TABLE 1-continued

The effect of different batches of thermostable RNase H on the C4 background and Net Percent Probe Cut in the presence or absence of hgDNA (200 ng) using chimeric probe ARK2 and genomic *M. tuberculosis* DNA target in the presence of *M. gordonnae* and SSB in CPT reactions.

| RNase H Batch Preparation | *M. gordonnae* C4 (%) | Net Probe Cut (%)[1] | *M. gordonnae* & hgDNA C4 (%) | Net Probe Cut (%)[2] |
|---|---|---|---|---|
| A11-1 | 3 | 73 | 9 | 43 |
| A12-1 | 0 | 84 | 7 | 13 |

[1] Net Percent Probe Cut was obtained by subtracting the *M. gordonnae* C4 background from the total Percent Probe Cut as described in Example 2.
[2] Net Percent Probe Cut was obtained by subtracting the hgDNA & *M. gordonnae* C4 background from the total Percent Probe Cut as described in Example 2

Example 4

Identification of Components Causing Variation in CPT Reactions

The following example shows the surprising correlation of the variability in CPT reactions with the presence of contaminating protein components in the RNase H batch preparations.

Each of the RNase H enzyme batches used in Example 3 were analyzed for their purity by resolving them electrophoretically using 20% Phast SDS-PAGE (Pharmacia) relative to known molecular mass protein standards (6.2 kDa to 16.9 kDa). After electrophoresis the proteins in the gel were stained with Coomasie Blue.

Figure 2:
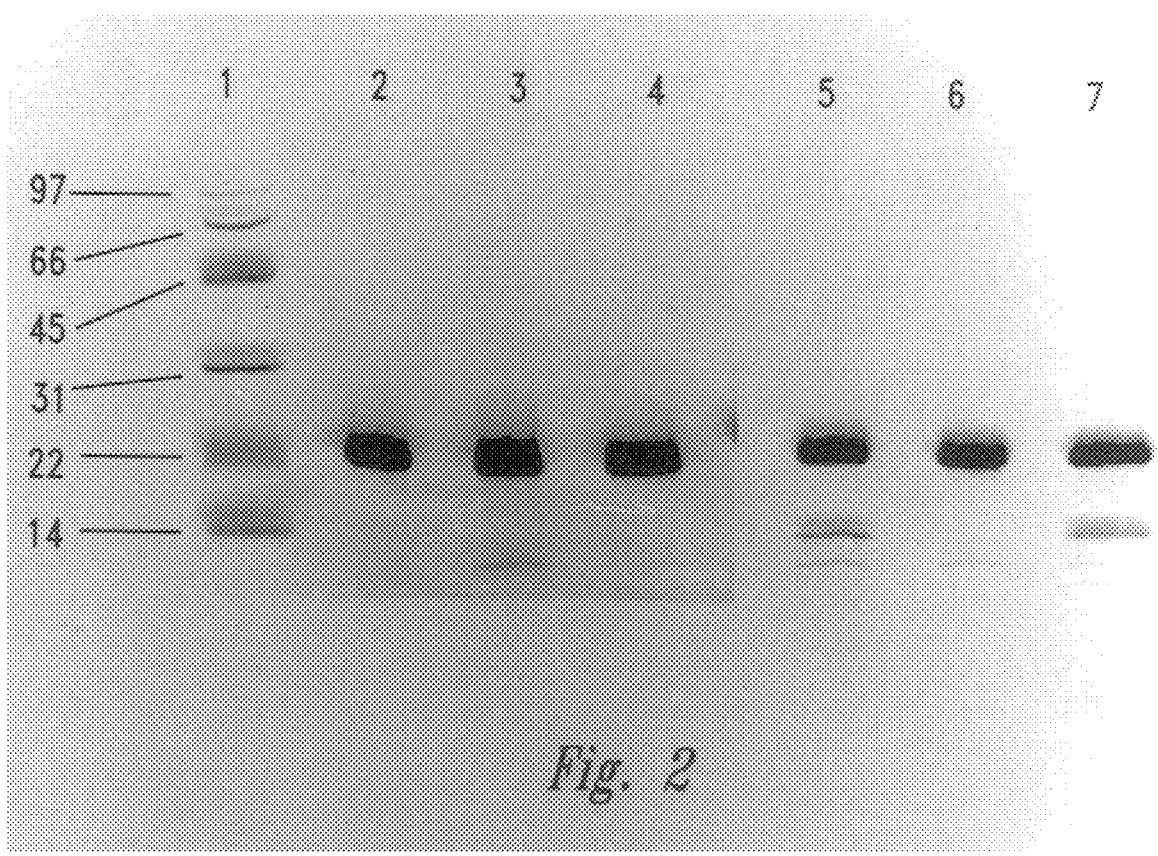
FIG. 2 is a depiction of the proteins from different *T. thermophilus* RNase H enzyme batches separated on a 20% sodium dodecyl sulfate polyacrylamide gel by electrophoresis (SDS-PAGE) and stained with Coomassie Blue. Lane 1 contains the low molecular mass standards; Lanes 2 to 7 contain the *T. thermophilus* RNase H enzyme batches A10-1, A11-1, A12-1, A8-1, A7-1, and A6-1, respectively.

FIG. 2 proteins from different *T. thermophilus* RNase H enzyme batches analyzed by SDS-PAGE. As expected, the main RNase H protein band resolved at approximately 19 kDa. However, there were variable amounts of additional smaller protein bands in the range of approximately 9 to 14 kDa that were also observed. Two of the minor bands were approximately 10 kDa and 13 kDa relative to molecular mass standards. For each of the enzyme batches, the protein components and relative concentrations were compared to the relative amount of probe cleaved in the CPT reactions of Example 3.

The combined results of this experiment and Example 3 are summarized in Table 2 below. The RNase H batch preparation numbers have been reorganized according to the relative purity of the preparation and the enzyme batches are ranked from 1, for approximately greater than 95% purity, to 6, for approximately 90% purity. Surprisingly, the results in Table 2 show that there was an unexpected correlation between the presence of these proteins in the enzyme batches and the Net Percent Probe Cut generated in each CPT reaction. There is a concomitant increase in the Net Percent Probe Cut with the increase in relative amount of the "10 kDa" and "13 kDa" proteins present in the RNase H enzyme batches. These proteins are termed accessory proteins of RNase H.

The differences between these RNase H batches were not discovered earlier due to one or more of the following: each of the final RNase H batch preparations were analyzed by silver staining, which did not stain these impurities efficiently; all these batches were tested in the simple CPT system, i.e., without added heterologous nucleic acids, and each batch had small variation which was not significant; the level of RNase H induction varied between batches and finally the fractions collected during the purification varied from batch to batch depending on the level of RNase H induction.

TABLE 2

Relative purity of different batches of enzymes, relative amounts of "10 kDa" and "13 kDa" proteins and comparison of Net Percent Probe Cut in presence or absence of 200 ng of hgDNA.

| RNase H Enzyme Batch | Relative Purity | Relative amount of "10 kDa" protein[1] | Relative amount of "13 kDa" protein[1] | Net Probe Cut (%)[2] No hgDNA | Net Probe Cut (%)[3] with hgDNA |
|---|---|---|---|---|---|
| A10-1 | 1 | − | − | 83 | 16 |
| A12-1 | 2 | − | + | 84 | 13 |
| A7-1 | 3 | ++ | ++ | 70 | 36 |
| A11-1 | 4 | + | +++ | 73 | 43 |
| A6-1 | 5 | +++ | ++ | 80 | 47 |
| A8-1 | 6 | ++++ | ++ | 77 | 50 |

[1]The presence and relative abundance of each protein in an enzyme batch is indicated by the number of plus signs (+). The absence of protein is indicated by a negative sign (−).
[2,3]The Net Percent Probe Cut results are from Table 1, Example 3.

The above example demonstrates that the presence and quantities of accessory proteins, such as the "10 kDa" and "13 kDa" proteins, present in partially purified RNase H preparations, correlated with Net Percent Probe Cut in samples that contained heterologous DNA. It was also unexpected that relatively pure RNase H, i.e., with minimal or no accessory proteins, had reduced or minimal activity in CPT reactions in the presence of heterologous nucleic acids. Therefore these accessory proteins appear to have a beneficial effect in the CPT reaction.

Example 5
Partial Purification of Accessory Proteins

The following example demonstrates partial purification of accessory proteins.

The "10 kDa" accessory protein was isolated by a modification of Bekkaoui et al., supra. After the step of applying protein solution to the second 5 ml phosphocellulose and in the absence of urea, protein elution was performed with a gradient 0.3 to 1.0 M NaCl in 10 mM sodium acetate (pH 5.5). The protein fractions were concentrated with a micro-concentrator (Centricon 10, Amicon, Beverly, Mass.) and applied to a Superose 12 column (Pharmacia Biotech) using acetate buffer (20 mM sodium acetate pH 5.5, and 150 mM NaCl). The "10 kDa" protein eluted after the main RNase H protein peak and was concentrated with the micro-concentrator. The protein concentration was determined by Bradford method (Bradford, *Anal. Biochem.* 72:248–254, 1976). The above method allows for the purification of the accessory protein to approximately 90% purity. The "13 kDa" protein was also partially purified (data not shown).

These proteins were analyzed by SDS PAGE as described previously and the putative molecular mass was confirmed to be approximately 10 kDa and 13 kDa, respectively.

Example 6
Improvement of CPT Reaction With Partially Purified Accessory Protein The followings example confirms that addition of partially-purified "10 kDa" accessory protein to the reaction mixture containing purified RNase H improves the CPT reaction in the presence of heterologous DNA.

In this experiment the effect of increased concentrations of partially purified "10 kDa" protein in CPT reaction mixtures containing relatively pure RNase H or partially purified RNase H, and hgDNA were tested. The chimeric probe ARK2 (SEQ ID NO: 1) was synthesized as described in Example 1 and labeled as described in Example 2. The target genomic *M. tuberculosis* was prepared as described by the method of Beggs et al., supra. Partially-purified RNase H A8-1 and relatively pure RNase H A12-1 were produced and analyzed for purity as described in Example 3. The partially purified "10 kDa" protein was prepared as described in Example 5 and 100 ng to 1000 ng of the protein was tested in CPT reactions. The CPT reactions and analysis were carried out essentially as described in Example 2 with the following exceptions: 3000 cpm of ARK2 probe, 2.5 ng of *M. tuberculosis* genomic DNA ($5 \times 10^5$ cell equivalents of DNA), 4 µg RNase H from the specified batch preparation, 1 µg of *E. coli* SSB, 200 ng hgDNA, in Tris cycling buffer in a final reaction volume of 40 µl.

Table 3 below, shows the results of the effect of increased concentration of "10 kDa" protein in CPT reaction with partially purified and purified RNase H. There was a minimal increase in the Net Percent Probe Cut when SSB was used as the only additive to the reaction containing purified RNase H. Addition of "10 kDa" protein ranging from 100 ng to 1000 ng resulted in an increase of approximately 30% CPT product. In contrast, there was no increase in Percent Probe Cut when "10 kDa" protein was added to samples containing partially purified RNase H. In fact at the highest concentration tested, the Percent Probe Cut decreased by 25%. These results indicate that "10 kDa" protein addition improves the CPT reaction when purified RNase H is used in the presence of hgDNA. Semi-purified RNase H already contains "10 kDa" protein and other accessory proteins (see Examples 3 and 4) and therefore, further addition of "10 kDa" protein to reaction mixture may not effect the reaction or may actually inhibit the CPT reaction. Therefore the effect of "10 kDa" protein in a reaction seems to be concentration dependent. Additionally, it may also depend on the concentration of nucleic acids present in the sample tested.

TABLE 3

Addition of partially purified "10 kDa" protein to CPT reaction mixtures containing partially purified or purified *T. thermophilus* RNase H and its effect on the Percent Probe Cut for detection of *M. tuberculosis* DNA target using ARK2 probe.

| "10 kDa" Protein (ng) | Partially purified RNase H (A8-1) Probe Cut (%) | Purified RNase H (A12-1) Probe Cut (%) |
|---|---|---|
| 0 | 66 | 20 |
| 100 | 66 | 51 |
| 250 | 66 | 55 |
| 1000 | 41 | 49 |

Previously it has been shown that the inhibition of CPT reaction by heterologous DNA could be improved by increasing the concentration of partially-purified RNase H used in the reaction (data not shown). The results from the above experiment and Example 4, suggests that the components responsible, at least in part, for the improvement in the CPT reaction are the accessory proteins that were co-purified with RNase H.

The above example confirms that the accessory proteins present in partially purified RNase H are responsible for improving the CPT reaction in the presence of hgDNA.

Example 7
Preparation of Purified and Partially Purified Thermostable RNase H The following example shows the controlled method utilized for preparing purified and partially purified thermostable RNase H.

The method for producing partially-purified and purified *T. thermophilus* RNase H was based on Bekkaoui et al., supra, with the following modifications. The procedure was scaled up to a 6 l fermenter from 1 l flask. To further increase the yield of the preparation, protein from a total of 36 l were processed in 12 l lots and pooled before the gel filtration by Superdex-75 (Pharmacia). The gel filtration was carried out using 20 mM NaAc pH 5.5, 150 mM NaCl buffer at a flow rate of 1 ml/minute. Fractions of 1 ml were collected over a period of 120 minutes. For the preparation of A24-1, fractions 14 to 32 were collected and pooled. The fractions in the shoulder of the peak contained the accessory proteins. For the preparation of A26-1, the protein samples were treated essentially as A24-1 batch, except that only fractions 19 to 27 were collected and pooled. These column fractions contained RNase H.

Figure 3:
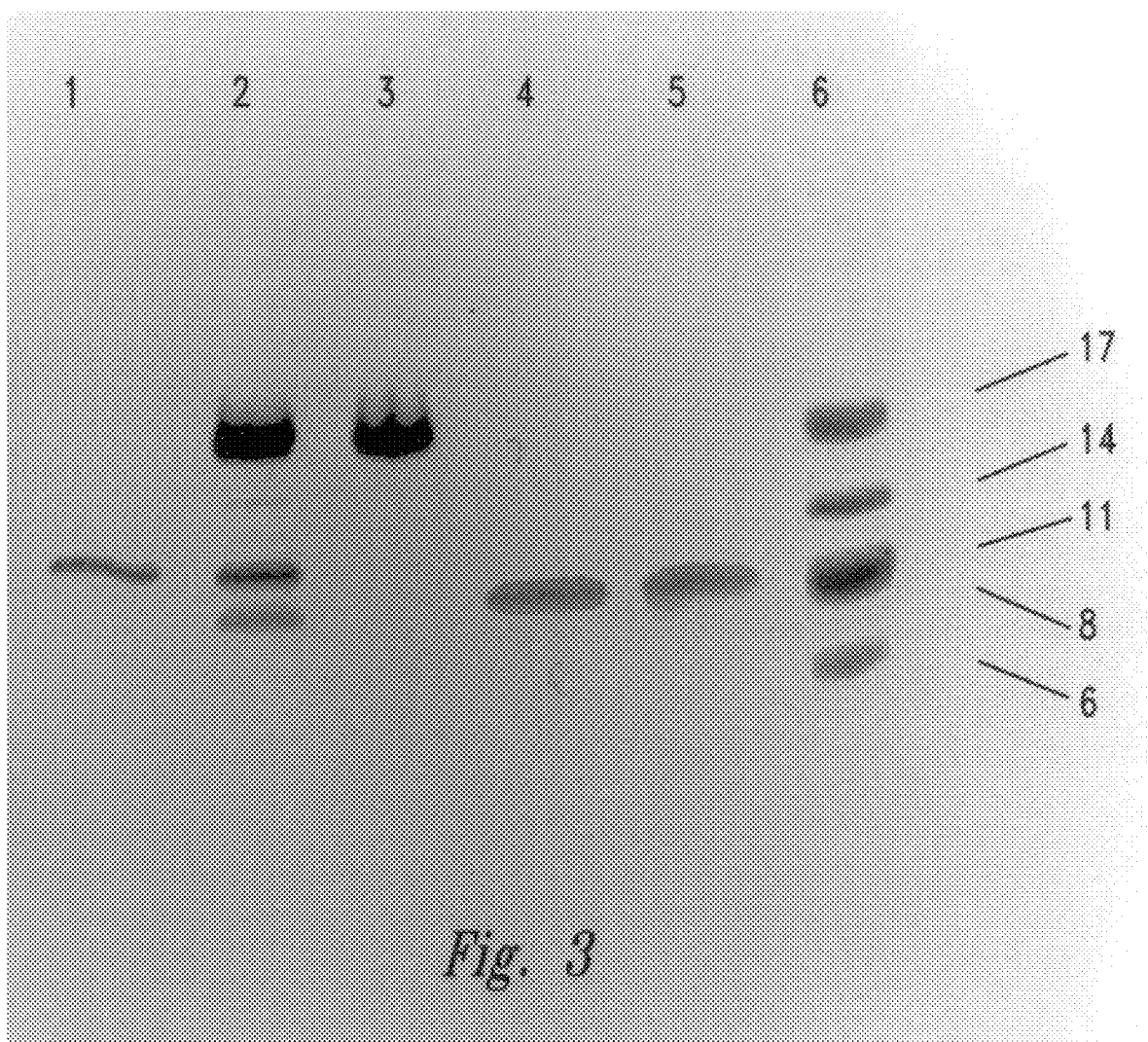
FIG. 3 is a depiction of the proteins from purified and partially-purified *T. thermophilus* RNase H enzyme which was cloned and expressed in *E. coli*, purified accessory proteins from the RNase H preparations and *E. coli* L34 ribosomal protein, separated by 20% SDS-PAGE and stained with Coomassie Blue. Lane 1, purified S19 ("13 kDa" protein); Lane 2, partially purified RNase H batch A24-1; Lane 3, relatively pure RNase H batch A26-1; Lane 4, purified L34 protein, Lane 5, *E. coli* L34 protein and Lane 6, low molecular mass standards.

FIG. 3 depicts the Coomassie Blue stained SDS-PAGE of the partially-purified RNase H, A24-1 (lane 2) and purified RNase H, A26-1 (lane 3). As can be seen from the gel, the purified RNase H sample showed one major band of RNase H with relative molecular mass of approximately 19 kDa. The partially-purified RNase H sample showed the major RNase H band, and in addition, two minor bands of the "13 kDa", "10 kDa" accessory proteins and traces of other accessory proteins.

Example 8
Effect of Heterologous DNA in CPT Reaction

The following example demonstrates that increasing quantities of heterologous DNA in samples increases the background and decreases Percent Probe Cut in a standard CPT reaction.

The chimeric probe ARK2 (SEQ ID NO:1) and the synthetic target ARK2-95 (SEQ ID NO: 3) were synthesized and the probe labeled as described in Example 1 and 2. The purified RNase H A26-1 and the partially-purified RNase H A24-1 were prepared as described in Example 7. The hgDNA was titrated using 0 to 800 ng final concentration. The CPT reaction and analysis were carried out essentially as described in Example 2 except for the following: 0.6 fmol (2000 cpm) of ARK2 probe, $1 \times 10^{-5}$ pmol of target ARK2-95, 8.0 mM $MgCl_2$, 1 μg of purified RNase H (A26-1) or partially-purified RNase H (A24-1), 0.025% Triton X-100®, 0.5 mM ethylenebis(oxyethylenitrilo)-tetraacetic acid (EGTA), 50 mM Tris, pH 8.1 in a 30 μl final reaction volume.

The results of the above experiment are summarized in Table 4. Briefly, in the absence of hgDNA, sample containing purified RNase H had greater Net Percent Probe Cut compared to sample containing partially-purified RNase H. However, upon the addition of 4 ng of hgDNA to the samples containing purified RNase H, the C4 background increased. Addition of greater than 4 ng of hgDNA decreased both the background and the Percent Probe Cut to the levels of non-detection of the target. Samples containing partially-purified RNase H tolerated between 100 to 200 ng hgDNA and above 200 ng, both the background and Percent Probe Cut decreased to the point where there was no detection of the target.

TABLE 4

The effect of increased concentrations of hgDNA in samples used for CPT detection of ARK2-95 (SEQ ID NO:3) target, using purified (A26-1) and partially purified (A24-1) RNase H.

| | | hgDNA (ng) | | | | | | |
|---|---|---|---|---|---|---|---|---|
| | | 0 | 4 | 40 | 100 | 200 | 400 | 800 |
| RNase H A24-1[1] | Probe Cut (%) | 73 | 82.1 | 87.1 | 65.3 | 33.5 | 15.8 | 7.7 |
| | C4 background (%) | 2.5 | 12 | 31.7 | 29.3 | 29.8 | 21.9 | 7.3 |
| | Net Probe Cut (%) | 70.5 | 70.1 | 55.4 | 36 | 3.7 | −6.1 | 0.4 |
| RNase H A26-1[2] | Probe Cut (%) | 88.6 | 89.9 | 15 | 13.5 | 10.9 | 7.5 | 6.2 |
| | C4 background (%) | 5.4 | 20.7 | 14.6 | 12.9 | 10.9 | 7.4 | 6.3 |
| | Net t Probe Cut (%) | 83.2 | 69.2 | 0.4 | 0.6 | 0 | 0 | −0.1 |

[1]Partially purified RNase H
[2]Purified RNase H

The above example confirms that heterologous DNA increases the background and also decreases the Net Percent Probe Cut for samples containing both purified and partially-purified RNase H. CPT reaction carried out with partially-purified RNase H could tolerate greater concentrations of hgDNA compared to relatively pure RNase H.

Example 9
Purification and Characterization of the Accessory Proteins as Ribosomal Proteins The following example shows the further purification and amino acid sequence characterization of the accessory proteins, with the surprising results identifying the accessory proteins as E. coli ribosomal proteins.

The "10 kDa" protein was partially purified as described in Example 5 and the amino acid sequencing of the protein was carried out as follows. The protein was resolved on a 15% SDS-PAGE (Bio-Rad Mini-cell, Richmond Calif.) using a tricine buffer (100 mM Tris, tricine 100 mM, pH 8.3, 0.1% SDS). The proteins were then electroblotted to an Immobilon$^{SQ}$ membrane using glycine buffer (25 mM Tris Base, 192 mM glycine and 20% methanol). The membrane was stained with Coomassie Blue and the visualized protein bands were excised. Amino acid sequencing of the sample is carried out using Applied Biosystems 470A gas phase sequencer with on-line PTH-analyzer and 900A system controllers. Homology search with the Genebank sequences was carried out using the Blast/Align program (Altschul et al., *J. Mol. Biol.* 215:403–10, 1990).

Using the above method, the "10 kDa" was sequenced and the partial amino acid sequence is shown below in Table 5. Alignment of the partial amino acid sequence to the Genebank protein sequences showed 90% homology of the "10 kDa" with the first 21 amino acids of the L34 ribosomal protein from *E. coli*. The "13 kDa" protein was also purified and characterized (data not shown) and the sequence was found to match the S19 ribosomal protein from *E. coli* (Table 5).

TABLE 5

The following are partial amino acid sequences of the
"10 kDa" and "13 kDa" proteins followed by partial
amino acid sequences obtained from homology searching.

| Protein | Source | Amino acid Sequence |
| --- | --- | --- |
| 10 kDa | Partial Sequence[1] | X Lys Arg Thr Phe Gln Pro Ser Val Leu Lys Arg Asn Arg Ser X Gly Phe Arg Ala Arg (SEQ ID NO:8) |
| E. coli L34 | GeneBank | Met Lys Arg Thr Phe Gln Pro Ser Val Leu Lys Arg Asn Arg Ser His Gly Phe Arg Ala Arg (SEQ ID NO:9) |
| 13 kDa | Partial Sequence[2] | Arg Ser Leu Ala Gly Gly Pro Phe Ile Asp Leu His Leu Ile Lys Lys Val Glu (SEQ ID NO:10) |
| E. coli S19 | GeneBank | Arg Ser Leu Lys Lys Gly Pro Phe Ile Asp Leu His Leu Leu Lys Lys Val Glu(SEQ ID NO:11) |

[1]The first 21 amino acids of the "10 kDa" protein matched the amino acid sequence of ribosomal protein L34 from E. coli (X indicates amino acids that were not identified).
[2]The first 18 amino acids from the "13 kDa" protein sequence were 83% homologous to those of the S19 ribosomal protein from E. coli.

The following experiment was carried out to compare the electrophoretic profile of the purified S19, purified L34, synthetic L34 with partially purified and purified RNase H using 20% SDS-PAGE Phast system (Pharmacia). The electrophoresis was carried out according to the manufacturer's recommended procedure and the proteins were stained with Coomasie Blue. L34 was obtained from Dr. B. Cooperman (University of Pennsylvania, Philadelphia, Pa.). L34 was also synthesized, based on the published amino acid sequence of L34, by the Protein Service Laboratory (University of British Columbia, Vancouver, BC) and sequence was confirmed by amino acid analysis and Mass spectroscopy.

FIG. 3 shows the results of the gel electrophoretic profile of the *T. thermophilus* RNase H enzymes, purified S19, L34 and synthetic L34. The putative molecular mass of the two accessory proteins were determined to be approximately 10 kDa and 13 kDa relative to the low molecular mass standards. The L34 and "10 kDa" protein had the same profile and a putative molecular mass of approximately 10 kDa. It should be noted that the deduced molecular mass of the *E. coli* L34 from the amino sequence is approximately 5.4 kDa. The anomaly in molecular mass could be due to L34 having a high positive charge and an isoelectric charge of 13.5 estimated by the software program DNASIS (Hitachi, San Bruno, Calif.). This may also explain why the isolated accessory protein L34 migrated with lower mobility in SDS-PAGE and had a putative molecular mass of approximately 10 kDa according to Example 4. Majority of the ribosomal proteins are relatively basic and have high isoelectric points (Kaltschimdt, cited in Giri et al., supra), with a high content of basic amino acids. The molecular mass of L34 is 5.4 kDa with 46 amino acid residues, and S19 is 10.3 kDa with 91 residues (Wittmann-Liebold, cited in Giri et al., supra, Wittmann, cited in Giri et al., supra). Therefore it was concluded that the two isolated proteins from the partially purified thermostable RNase H preparations were L34 and S19 *E. coli* ribosomal proteins.

The above example demonstrated that the accessory proteins identified as the components responsible for the differences in the Net Percent Probe Cut of samples containing heterologous DNA in the CPT reactions using the different batches of RNase H enzymes, are ribosomal proteins of *E. coli*. These proteins were inadvertently present with RNase H preparations as part of the RNase H purification process. It has been known in the art that thermostable RNase H is responsible for cleaving RNA when in duplexed form with DNA, however, the fact that these ribosomal proteins improved CPT reaction when purified RNase H was used in the presence of heterologous DNA was an unexpected discovery.

Example 10

Effect of Yeast Ribosomal Proteins in CPT Reaction Decreasing Background Caused by Heterologous DNA The following example illustrates that the ribosomal proteins from other organisms besides *E. coli* improve CPT reaction in the presence of heterologous DNA using purified RNase H.

In this experiment the effect of crude yeast 60S ribosomal proteins (YRPs) and L34 were examined in CPT reactions containing relatively pure RNase H and hgDNA. The chimeric probe ARK2 (SEQ ID NO: 1) and the target ARK2T (SEQ ID NO:2) were synthesized as described in Example 1, partially-purified RNase H, A24-1 and purified RNase H, A26-1 were prepared as described in Example 8, crude yeast ribosomal proteins were obtained from Dr. Ross Nazar, University of Guelph, Guelph, ON, and were prepared by the method of Katschimdt & Wittman, *Anal Biochem* 36:401–412, 1970, purified L34 was prepared as described in Example 9. The CPT reaction and analysis were carried out under the following conditions: 0.6 fmol of ARK2 probe (SEQ ID NO: 1), $10^{-5}$ pmol of ARK2T target, 2.0 mM $MgCl_2$, 200 ng of hgDNA, 1 μg of partially purified or purified RNase H, 0.025% Triton X-100®, 50 mM Tris, pH 8.3 in a 20 μl final reaction volume. 200 ng of yeast ribosomal proteins, and 100 to 200 ng of purified L34 were tested in CPT reaction mixture containing purified RNase H.

Table 6 shows the results of the above experiment. Briefly, in the absence of any additives in the sample containing purified RNase H, the reaction was inhibited in the presence of hgDNA. Addition of 200 ng yeast ribosomal proteins reduced the inhibition caused by hgDNA when using purified RNase H. L34 ribosomal protein also improved Net Percent Probe Cut in the presence of hgDNA. It was also observed that the Net Percent Probe Cut increased with the increase in concentration of L34 in the sample containing purified RNase H. The level of improvement in purified RNase H containing 200 ng of YRP and 200 ng of L34 ribosomal protein was comparable to the partially-purified RNase H (A24-1). Ribosomal proteins do not catalyze the cleavage of chimeric probe in the absence of RNase H (data not shown) therefore indicating that these proteins have an unknown role in improvement of the CPT reaction.

TABLE 6

Effect of yeast ribosomal proteins (YRPs) and purified L34 ribosomal protein. Background observed in the presence of hgDNA and absence of target was subtracted.

| RNase H | Additive | C4 (%) | Net Probe Cut (%) |
|---|---|---|---|
| Partially purified (A24-1) | — | 44 | 43 |
| Purified (A26-1) | — | 30 | 0 |
| Purified (A26-1) | 200 ng YRPs | 35 | 40 |
| Purified (A26-1) | 100 ng L34 | 55 | 27 |
| Purified (A26-1) | 200 ng L34 | 41 | 47 |

[1]Net Percent Probe Cut (%) = Percent Probe Cut (%) - C4 background (%)

This example illustrates that the Net Percent Probe Cut can be improved in CPT reactions using purified RNase H in the presence of heterologous DNA by the use of ribosomal proteins from both prokaryotic and eukaryotic organisms.

Example 11
Effect of Ribosomal Proteins L34 in CPT Reaction in the Presence of Heterologous DNA The following example demonstrates the use of L34 ribosomal protein for improving CPT reaction in the presence of heterologous DNA.

Three experiments were carried out to examine the effect of L34 addition to CPT reactions in the presence of increasing concentration of heterologous DNA and using purified thermostable RNase H. The first experiment had no L34 added, the second had 200 ng of purified L34 and the third experiment had 400 ng of synthetic L34 added to the CPT reactions. It has been previously been shown that the synthetic L34 had similar effect to purified L34 (data not shown).

The chimeric probe ARK2 (SEQ ID NO: 1) and the target ARK2-95 (SEQ ID NO:3) were synthesized and the probe labeled as described in Example 1. The purified thermostable RNase H A26-1 was prepared as described in Example 8, purified and synthetic L34 were prepared as described in Example 9. The CPT reaction and analysis were carried out essentially as described in Example 2 with the following exceptions: 0.6 fmol ARK2 probe, $10^{-5}$ pmol dsARK2-T target, 1 µg of purified RNase H A26-1, 0 to 800 ng of hgDNA, 0.025% Triton X-100®, 8 mM MgCl$_2$, 50 mM Tris, pH 8.1 in a final reaction volume of 30 µl. The additives tested were: 0 ng, 200 ng purified L34 and 400 ng synthetic L34. The hgDNA with the spiked target dsARK2T were denatured at 90° C. for 5 min and then chilled on ice.

Table 7 is a compilation of the results from the three experiments. Briefly, in absence of L34 in the CPT reaction, the Net Percent Probe Cut decreased with increasing concentrations of hgDNA. The target was not detected at hgDNA concentrations of greater than or equal to 40 ng. CPT target detection was dramatically improved in the presence of 200 ng of purified L34 compared to the controls (no addition of L34), at all the different concentrations of hgDNA in the CPT reactions. Addition of 400 ng L34 showed an improvement in Net Percent Probe Cut compared to the controls. However, the Net Percent Probe Cut in the presence of 400 ng of L34 were lower for samples containing 0 to 200 ng of hgDNA, and higher for the samples containing 400 to 800 ng of hgDNA. Since there was no addition of SSB in these samples it can be concluded that the improvement of CPT reactions was due to L34 ribosomal protein and independent of SSB.

TABLE 7

The effect of L34 addition to CPT reaction in the presence of increasing concentrations of hgDNA and using purified *T. thermophilus* RNase H.

| | 0 ng | | 200 ng | | 400 ng | |
|---|---|---|---|---|---|---|
| hgDNA (ng) | C4 (%)[3] | Net Probe Cut[1] (%) | C4 (%) | Net Probe Cut (%) | C4 (%) | Net Probe Cut (%) |
| 0 | 5.4 | 83.2 | 2.7 | 86.1 | 3.2 | 18.0 |
| 4 | 20.7 | 69.2 | 8.8 | 78.7 | 3.6 | 53.6 |
| 40 | 14.6 | 0.4 | 8.6 | 59.3 | 9.1 | 47.5 |
| 100 | 12.9 | 0.6 | 10.0 | 40.4 | 10.8 | 32.4 |
| 200 | 10.9 | 0.0 | 17.1 | 39.0 | 14.1 | 23.7 |
| 400 | 7.4 | 0.0 | 12.1 | 5.4 | 32.4 | 14.4 |
| 800 | 6.3 | -0.1 | 6.0 | 1.0 | 14 | 7.2 |

[1]Probe Cut (%) - C4 background (%)

The above example demonstrates that L34 ribosomal protein improves CPT reaction in the presence of both low and high concentrations of heterologous DNA depending on the concentration of L34 used.

Example 12
Effect of Additives in Clean CPT System

The following example demonstrates that additives such as ribosomal proteins and spermine improve CPT reactions using different levels of target DNA in the absence of heterologous DNA. In particular, this experiment was designed to examine the effect of S19, L34 ribosomal proteins in CPT reaction for the detection of decreasing concentrations of target using purified RNase H in a clean system, i.e., in the absence of hgDNA.

The chimeric probe mecA945-29 (SEQ ID NO:4) and the target mecA945-29-T (SEQ ID NO:5) were synthesized and the probe labeled as described in Example 1. The purified RNase H A26-1 was prepared as described in Example 8, synthetic L34 was synthesized as described in Example 9, and S19 ribosomal proteins was purified as described in Example 9. The CPT reaction and analysis were carried out essentially as described in Example 2 with the following exceptions: 0.3 fmol of mecA945-29 probe, $10^{-4}$ to $10^{-6}$ pmol of mecA945-T target, 4.0 mM MgCl$_2$, 1 ng of purified RNase H (A26-1), 1.0% Triton X-100®, 10 mM PB, pH 6.4, in a final reaction volume of 10 µl. The additives tested were: 10 ng of L34, 10 ng of S19 and 0.2 mM spermine.

Table 8 summarizes the results of the above experiment. Briefly, the results indicate that addition of the ribosomal proteins or spermine to CPT reaction markedly improved Net Percent Probe Cut at all target levels and especially for $10^{-5}$ and $10^{-4}$ pmol concentrations compared to the control which had no additives.

TABLE 8

The effect of spermine, S19 and L34 on the Net Percent Probe Cut using synthetic target. Standard deviation (SD) is shown in the brackets.

| | Net Probe Cut (%), (SD) | | | |
|---|---|---|---|---|
| Target (pmol) | Control | Spermine 0.2 mM | S19 10 ng | L34 10 ng |
| 1 × $10^{-4}$ | 13 (1.4) | 53 (2.7) | 64 (18) | 46 (2.3) |
| 1 × $10^{-5}$ | 1.6 (0.2) | 7 (1.7) | 11 (5.4) | 6 (0.8) |
| 1 × $10^{-6}$ | 0 (0.1) | 1 (0.4) | 1 (0.2) | 1 (0.1) |

The above example demonstrates that under the experimental conditions, the ribosomal proteins, L34 and S19, and spermine improved the CPT reaction in clean system.

Example 13
Effect of Chelator in CPT Reaction in the Presence of Heterologous DNA The following example demonstrates that the chelator EGTA when incorporated in the cycling reaction buffer improved the Percent Probe Cut and reduced C4 background in the presence of heterologous DNA.

In this experiment the effect of EGTA was examined in the CPT reaction for detection of genomic *M. tuberculosis* DNA target, in the presence of hgDNA. The CPT reaction and analysis were carried out as described in Example 2 with the following exceptions: 1.5 fmole (3000 cpm/40 µl) of the chimeric probe ARK-2 (SEQ ID NO:1), 5×10$^5$ cell equivalent of *M. tuberculosis* DNA, 800 ng of hgDNA, 1.25 mM MgCl$_2$, 4.0 µg of purified RNase H A17-1, in a final reaction volume of 40 µl. The concentration range of EGTA tested ranged from 0.2 to 7.5 mM. *M. gordonnae* DNA was used as the non-specific DNA target control.

Table 9 summarizes the results of the above experiment. It was observed that the signal to noise ratio (S:N) increased with increasing concentration of EGTA. This was due to the greater decrease in the background (C4) compared the Percent Probe Cut decrease in the increasing concentrations of hgDNA in the sample. A similar improvement of CPT reaction has been observed with the use of EDTA (data not shown).

TABLE 9

Effect of EGTA in samples containing hgDNA in CPT reactions for detection of *M. tuberculosis* DNA using RNase H A17-1.

| | EGTA (mM) | | | | | | |
|---|---|---|---|---|---|---|---|
| | 0 | 0.2 | 0.5 | 0.9 | 1.9 | 3.8 | 7.5 |
| Probe Cut (%) | 76 | 57 | 59 | 48 | 48 | 30 | 19 |
| C4 Background (%) | 34 | 13 | 14 | 9 | 7 | 4 | 2 |
| Net Probe Cut (%) | 42 | 44 | 45 | 39 | 41 | 26 | 17 |
| S:N | 2.2 | 4.4 | 4.2 | 5.3 | 6.9 | 7.5 | 9.5 |

The above example demonstrates that EGTA improves the CPT reaction in the presence of heterologous DNA in the samples.

Example 14
Effect of Spermine and Chelators for Improving CPT Reaction in the Presence of Heterologous DNA The following example illustrates that combination of spermine and chelators reduce background due to heterologous DNA in CPT reaction.

Preliminary experiments were carried out for assessing the utility of various polyamines and chelators for reducing the background associated with the presence of heterologous DNA in CPT reactions using purified thermostable RNase H. Polyamines such as spermine, spermidine and ornithine (0.5 to 10.0 mM), and chelators EGTA (0.5 to 2.0 mM), and EDTA (50 µM to 1.0 mM) were tested in CPT reactions using 800 ng of hgDNA. The synthetic target and chimeric probe were ARK2-95 (SEQ ID NO:3) and ARK2 (SEQ ID NO:1), respectively. It was observed that the spermidine and ornithine, at the concentrations tested, did not improve the CPT reaction. Spermine and EGTA or EDTA were shown to improve cycling in the presence of hgDNA in the sample. Further titration experiments showed that 2 mM spermine and 0.5 mM EGTA resulted in improvement of the CPT reaction in terms of both the decrease in background and an increase in the Net Percent Probe Cut.

In the following experiment the effect of 0.5 mM EGTA, 2 mM spermine or a combination of 0.5 mM EGTA and 2 mM spermine were examined in CPT reactions containing increasing amounts of hgDNA. The chimeric probe ARK2 (SEQ ID NO:1) and the double stranded target ARK2-95 (dsARK2-95; SEQ ID NO:3), were synthesized and the probe labeled as described in Example 1. The purified thermostable *T. thermophilus* RNase H (batch A26-1) was prepared as described in Example 8. The CPT reactions were carried out essentially as described in Example 2 with the following exceptions: 0.6 fmol ARK2 probe, 10$^{-5}$ pmol dsARK2-95, 1 µg of purified RNase H, 0 to 800 ng hgDNA in Tris-CB, pH 8.1, to final reaction volume of 30 µl. Prior to the addition of probe and enzyme, the hgDNA with the spiked dsARK2T target were denatured at 90° C. for 5 minutes then chilled on ice.

Figure 4A:
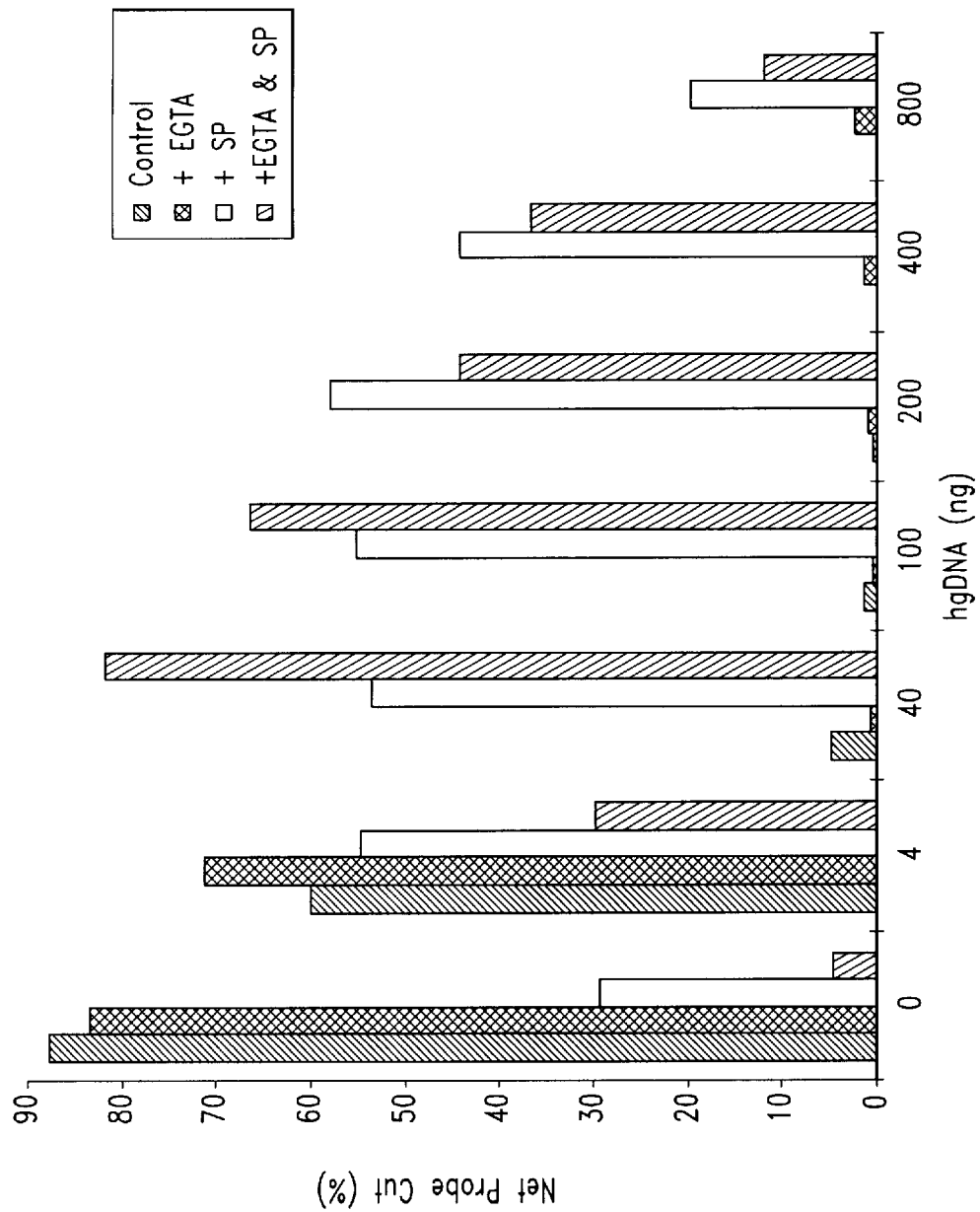
FIGS. 4A and 4B depict two histograms showing the Net Percent Probe Cut and Signal to Noise ratios obtained from the experiment testing the effect of ethylenebis (oxyethylenitrilo)-tetraacetic acid (EGTA, 0.5 mM) and spermine (2 mM, SP) in CPT reaction for detecting synthetic target sequence ARK2-95 (SEQ ID NO: 3) with chimeric probe ARK2 (SEQ ID NO: 1) in the presence of heterologous DNA. The EGTA and spermine were tested independently and together in CPT reactions with hgDNA ranging from 0 to 800 ng.
Figure 4B:
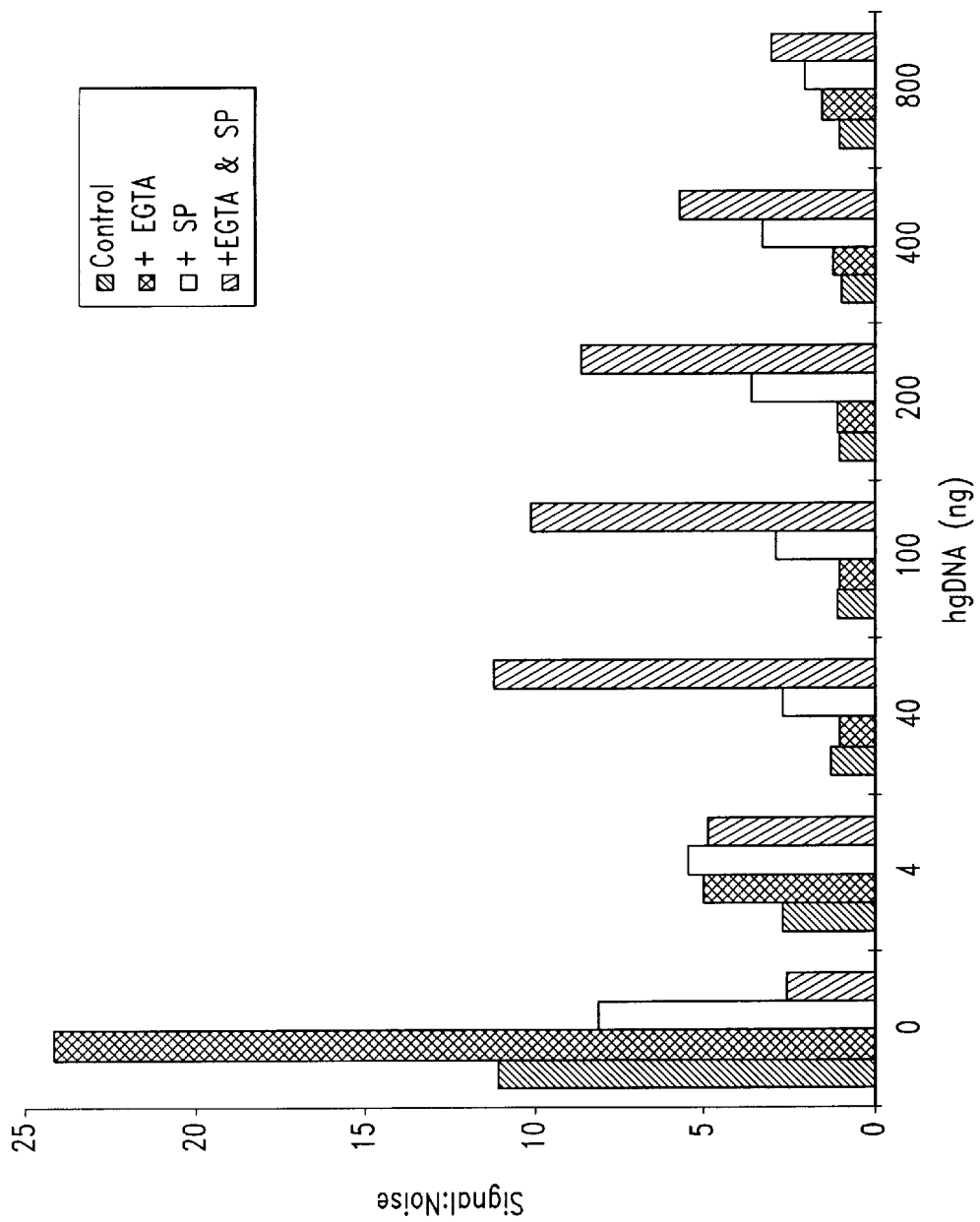

Table 10 summarizes the results of the above experiment and shows the effect of EGTA, spermine and the combination of spermine and EGTA on the C4 background and the Percent Probe Cut in CPT reactions with increasing concentrations of hgDNA. FIG. 4 shows the Net Percent Probe Cut and signal to noise ratio based on the results from Table 10. In samples containing no additives, detection of the target by CPT reaction was only possible in the presence of up to 4 ng of hgDNA (FIG. 4). In the presence of 0.5 mM EGTA the C4 background decreased compared to control (Table 10), however, detection was not possible in samples that contained greater than 4 ng of hgDNA due to low signal to noise ratio (FIG. 4). In these samples there was little difference between Percent Probe Cut and the C4 background (Table 10).

Use of 2 mM spermine markedly improved detection of the target in CPT reactions in the presence of hgDNA tested 4 ng to 800 ng (FIG. 4). Both the Percent Probe Cut and, to a lesser degree, the C4 background increased in the presence of spermine (Table 10), thereby resulting in a signal to noise ratio that that allowed for the detection of the target (FIG. 4). Reactions with spermine had approximately 1.4 to 2.7 times greater S:N compared to EGTA in samples containing 40 to 800 ng of hgDNA (FIG. 4).

A combination of EGTA and spermine in samples that contained high concentrations of hgDNA resulted in an unexpected and a significant improvement in detection of the target by CPT. The combined effect of spermine and EGTA resulted in low background (6 to 8%) in the presence of hgDNA. The background values in the presence of combined EGTA and spermine were lower than with either 0.5 mM EGTA or 2 mM spermine. It was surprising that this combination of additive resulted in a maximum Net Percent Probe Cut or signal to noise ratio in the presence of 40 ng of hgDNA, which was comparable to sample containing no hgDNA (FIG. 4). The amount of Percent Probe Cut generated in the presence of EGTA and spermine gradually decreased with increasing concentrations of hgDNA (Table 10), but the decrease in the background was relatively greater and therefore, the signal to noise ratio allowed for the detection of target in samples that contained up to 800 ng of hgDNA (FIG. 4).

These experimental results show that the CPT reactions for detecting nucleic acid targets that were previously inhibited by the presence of hgDNA, can now be overcome by the unexpected and surprising combination of EGTA and spermine in the reactions. These additives allow for detection of the target by CPT reaction in the presence of hgDNA as high as 800 ng.

TABLE 10

The effect of EGTA (0.5 mM), spermine (2 mM) and combination of EGTA (0.5 mM) and spermine (2 mM) on the C4 background and Percent Probe Cut generated in CPT reaction in the presence of increasing concentrations of hgDNA using purified RNase H.

| hgDNA | C4 (%)[1] | | | | Probe Cut (%)[2] | | | |
| --- | --- | --- | --- | --- | --- | --- | --- | --- |
| (ng) | Control[3] | EGTA | SP[4] | EGTA&SP | Control | EGTA | SP | EGTA&SP |
| 0 | 8.7 | 3.6 | 4.1 | 2.8 | 96.5 | 87 | 33.3 | 7.3 |
| 4 | 35.5 | 17.8 | 12.2 | 7.7 | 95.4 | 89 | 66.9 | 37.5 |
| 40 | 16.7 | 12.3 | 31.0 | 8.0 | 21.5 | 13 | 84.6 | 89.7 |
| 100 | 12.9 | 10.3 | 28.8 | 7.3 | 14.3 | 10.8 | 84.1 | 73.8 |
| 200 | 10.2 | 8.2 | 22.3 | 5.8 | 10.7 | 9.2 | 80.2 | 50.1 |
| 400 | 8.7 | 6.1 | 19.3 | 7.8 | 8.2 | 7.5 | 63.5 | 44.5 |
| 800 | 7.2 | 4.6 | 18.4 | 6.0 | 7.2 | 7 | 38.1 | 18 |

[1] background due to probe cleavage in presence of hgDNA
[2] Total probe cleavage
[3] No additives
[4] SP refers to spermine The above example demonstrates that the combination of spermine and EGTA was highly effective in improving CPT reaction using purified RNase H and allowed detection of nucleic acid target molecules in presence of both high and low concentrations of heterologous DNA.

Example 15
Effect of Combination of L34 and Spermine in CPT Reactions Containing Heterologous DNA The following example demonstrates that the combination of L34 and spermine improves the CPT reaction for detection of target in increasing concentration of hgDNA and also improves the sensitivity using decreasing concentration of target nucleic acid.

In the first experiment spermine and combination of spermine with L34 were tested in samples containing hgDNA ranging from 100 to 400 ng using the probe ARK2 (SEQ ID NO:1), genomic M. tuberculosis DNA target and purified RNase H (A26-1).

The chimeric probe ARK2 (SEQ ID NO:1) was synthesized as described in Example 1 and labeled as described in Example 2. Genomic M. tuberculosis DNA target was prepared as described by Beggs et al., supra. The purified RNase H A26-1 was prepared as described in Example 8.

The CPT reactions and analysis were carried out essentially as described in Example 2 except for the following: 0.6 fmol of ARK2 probe, $1 \times 10^{-5}$ pmol of ARK2-95 (SEQ ID NO:3), 8.0 mM $MgCl_2$, 1 µg of purified RNase H (A26-1), 0.025% Triton X-100®, 0.5 mM EGTA, 50 mM Tris, pH 8.3, in a final reaction volume of 20 µl final.

In the second experiment the sensitivity of the assay was examined using ARK2-95 target ranging from $1 \times 10^{-5}$ pmol to $2 \times 10^{-7}$ pmol, in the presence of 400 ng of hgDNA, and using purified RNase H (A26-1). The CPT reactions and analysis were carried out essentially as described in Example 2 except for the following: 0.6 fmol of ARK2 probe, specified concentration of genomic DNA, 8.0 mM $MgCl_2$, 1 µg of purified RNase H (A26-1), 0.025% Triton X-100®, 0.5 mM EGTA, 50 mM Tris, pH 8.3, in a final reaction volume of 30 µl final.

The results of the first experiment are summarized in Table 11. Briefly, the results confirm previous observations that addition of spermine improves the CPT reaction in samples containing hgDNA. For 100 ng to 400 ng the signal to noise ratio ranged from 7.6 to 6.3. However, when spermine was combined with L34 and tested in similar ranges of hgDNA, the signal to noise was greater and ranged from 11.3 to 15.7. Even though the specific probe cleavage was lower for the combination of additives, compared to spermine alone. It was interesting to note that the C4 background was reduced approximately 2 fold in these samples.

TABLE 11

The effect of spermine (2 mM) and the combination of spermine (2 mM) and L34 (200 ng) in samples in CPT reaction containing increasing concentrations of hgDNA.

| | hgDNA | | | | | | | |
| --- | --- | --- | --- | --- | --- | --- | --- | --- |
| | 100 ng | | 200 ng | | 300 ng | | 400 ng | |
| Additives | SP | SP + L34 | SP | SP + L34 | SP | SP + L34 | SP | SP + L34 |
| Probe Cut (%) | 87.1 | 77 | 83.7 | 75.4 | 82.6 | 81.6 | 79.6 | 76.3 |
| C4 background (%) | 11.5 | 5 | 11.8 | 6.7 | 11.3 | 5.2 | 12.6 | 5.9 |
| Net Probe Cut (%) | 75.6 | 72 | 71.9 | 68.7 | 71.3 | 76.4 | 67 | 70.4 |
| S:N | 7.6 | 15.4 | 7.1 | 11.3 | 7.3 | 15.7 | 6.3 | 12.9 |

The results of the second experiment testing the sensitivity of the CPT reaction in the presence of 400 ng of hgDNA are shown in Table 12. Briefly, the combination of spermine and L34 increased sensitivity of the CPT detection to a greater degree than spermine by itself. In the lowest con centration of the target tested, $2\times10^{-7}$ pmol, the signal to noise ratio was approximately 2.

TABLE 12

The effect of spermine (2 mM) and the combination of spermine (2 mM) and L34 (200 ng) in samples in CPT reaction in the presence of hgDNA and containing decreasing concentrations of ARK2-95 target.

| | Target Concentration | | | | | |
|---|---|---|---|---|---|---|
| | $1 \times 10^{-5}$ pmol | | $1 \times 10^{-6}$ pmol | | $2 \times 10^{-7}$ pmol | |
| Additive | SP | SP + L34 | SP | SP + L34 | SP | SP + L34 |
| Probe Cut (%) | 82.6 | 65.9 | 33.0 | 25.4 | 17.6 | 11.2 |
| C4 background (%) | 11.5 | 5.9 | 11.5 | 5.9 | 11.5 | 5.9 |
| Net Probe Cut (%) | 71.1 | 60.0 | 21.5 | 19.5 | 6.1 | 5.3 |
| S:N | 7.2 | 11.2 | 2.9 | 4.3 | 1.5 | 1.9 |

The above example demonstrates that the combination of spermine and ribosomal protein, L34, increased the signal to noise ratio and improved the sensitivity of CPT detection in the presence of heterologous DNA.

Example 16
Determining Methicillin Resistance Status of Staphylococcus aureus by Detection of mecA Gene Using CPT Reaction The following example demonstrates the utility of chimeric probe mecA945-29 (SEQ ID NO:4) and the effectiveness of spermine and EGTA in CPT reaction for the detection of the mecA gene from crude lysates of S. aureus isolates.

This experiment was designed to examine the effect of spermine and EGTA in the CPT reaction for detection of the mecA gene in MRSA isolates using crude lysates. The additive concentrations tested were 1 mM EGTA, 2 mM spermine or a combination of 1 mM EGTA and 2 mM spermine.

For this experiment the MRSA (ATCC 33592, American Type Culture Collection, Rockville, Md.) and MSSA (ATCC 11632) isolates were grown on trypticase soy agar (TSA) plates with 5% sheep blood (PML Microbiologics, Richmond, BC) at 37° C. overnight. A sterile swab was used to remove the colonies from the TSA plate followed by resuspension of the cells in 2 ml of 0.05% Triton X-100® in 20 mM TES buffer (pH 6.8). The cell suspensions were then adjusted to McFarland #5 standard cell density (approximately $1.5\times10^9$ cells/ml). Fifty µl of the cell suspensions (approximately $7.5\times10^7$ cells) were then transferred to microcentrifuge tubes. Lysis of the cells was carried out with the addition of achromopeptidase (Wako Bioproducts, Richmond, Va.) to a final concentration of 150 units/ml per sample. The suspensions were mixed and incubated at 37° C. for 20 minutes.

The chimeric probe mecA945-29 was synthesized as described in Example 1 and labeled as described in example 2 with the following exceptions. A single tube of RTG is resuspended in 15 µl of water. One pmol of probe is combined with 5 µl of $\gamma$-$^{32}$P ATP and 3 µl of RTG. The final volume is adjusted to 10 µl with water and incubated at 37° C. for 30 minutes. The unincorporated $\gamma$-$^{32}$P ATP is separated from the kinased probe by using a G50 Nick column (Pharmacia). The recovered probe is adjusted to 0.1× in SSC buffer (15 mM NaCl, 1.5 mM sodium citrate, pH 7.0) and stored at −20° C. Thermostable RNase H was produced as described in Example 7.

CPT reactions and analysis were carried out as in Example 2 except for the following: The CPT reaction was carried out by adding in order, the following: TES cycling buffer, chimeric labeled probe, RNase H to give a cycling cocktail, which is then added to the denatured sample to be tested. The final cycling reaction mixture contained 1.8 fmol mecA945-29 chimeric probe, Fifty µl of nucleic acid as crude lysate target, 3.3 µg RNase H in TES cycling buffer (TES-CB) which has the following final concentration: 0.05% Triton X-100®, 4 mM $MgCl_2$, 20 mM TES buffer, pH 6.8. Fifty µl of crude lysates samples were heat denatured in a heating block at 95° C. for 5 minutes, and then directly transferred to a 58° C. water bath (reaction temperature was 56° C.). The reaction cocktail (50 µl) was immediately added and the incubation was continued for an additional 20 minutes.

At the end of incubation, an equal volume of loading dye containing 40 mM PB (100 µl) was added to the samples in the water bath. The samples were then transferred to a 95° C. heating block for 5 minutes. Samples were spun down briefly and 20 µl was loaded onto an acrylamide gel for electrophoresis.

Table 13 summarizes the results of the effect of spermine and EGTA in CPT reactions for detection of the mecA gene from MRSA lysates. Briefly, it was observed that in the absence of spermine or EGTA there was no differentiation between the MRSA and MSSA isolates due to the high C4 background. The addition of EGTA alone reduced the Percent Probe Cut in both MRSA and MSSA, but still did not permit the differentiation between the two. Addition of spermine alone to the CPT reaction permitted the detection of MRSA by lowering C4 background, which resulted in a signal to noise ratio of approximately 5. Addition of both EGTA and spermine into the CPT reaction dramatically improved detection of the target. As shown in Table 1, there was a major reduction in the C4 background and mecA MRSA could be detected with an impressive signal to noise ratio of 20. These results clearly indicate the necessity of adding both spermine and EGTA to the cycling reaction in order to obtain clear differentiation between MRSA and MSSA isolates.

TABLE 13

The effect of spermine and EGTA in CPT reactions for detection of mecA gene from crude lysates of MRSA.

| EGTA (mM) | Spermine (mM) | C4 (MSSA) Background (%) | MRSA Probe Cut (%) | MRSA Net Probe Cut (%) | S:N |
|---|---|---|---|---|---|
| — | — | 84 | 77 | 0 | — |
| 1 | — | 21 | 22 | 1 | 1.0 |
| — | 2 | 15 | 71 | 56 | 4.8 |
| 1 | 2 | 2.5 | 51 | 48 | 20.0 |

The above example demonstrates that the combined use of the additives spermine and EGTA resulted in significant improvement of signal to noise ratio for detection of the mecA gene in crude lysates by CPT reaction, compared to the use of spermine or EGTA by itself.

Example 17
Clinical Screening for Methicillin Resistant Staphylococcal Isolates by Detection of the mecA Gene Using CPT Reaction The following example demonstrates the successful use of isotopically labeled chimeric probe and the additives, spermine and EGTA, in CPT reactions for the detection of mecA gene from crude lysates of staphylococcal clinical isolates.

This experiment examines the use of $^{32}$P labeled chimeric probe mecA945-29 (SEQ ID NO:4) and the combination of spermine (2.0 mM) and EGTA (1.0 mM) in CPT reaction for the detection of the mecA gene from crude lysates of 285 staphylococcal isolates. These isolates were from the following sources: Wishart Memorial Hospital (Indianapolis, Ind.), Cleveland Clinic Foundation (Cleveland, Ohio), Vancouver General Hospital (Vancouver, BC) and 25 reference strains. In total there were 238 S. aureus and 47 S. epidermidis isolates.

The crude lysate preparations, probe synthesis, CPT procedure and analyses were carried out as described in Example 16, except that the cells were picked from the TSA blood plate with a 1 μl plastic loop (PML Microbiological, Richmond, BC, Canada) resuspended in 50 μl of 0.05% Triton X-100® in 20 mM TES buffer (pH 6.8) and lysed with the addition of achromopeptidase (Wako Bioproducts) as described in Example 4. The DNA was heat denatured at 95° C. for 5 minutes prior to use. The experiment was carried out as an operator blind study. The isolates were also tested with conventional oxacillin screening agar (PML Microbiological), Kirby-Bauer Disc diffusion, minimal inhibitory concentration (MIC) using E-Test with 4% NaCl Meuller-Hinton and S. aureus were tested with the BBL® Crystal™ MRSA ID test (Becton Dickinson).

Figure 5:
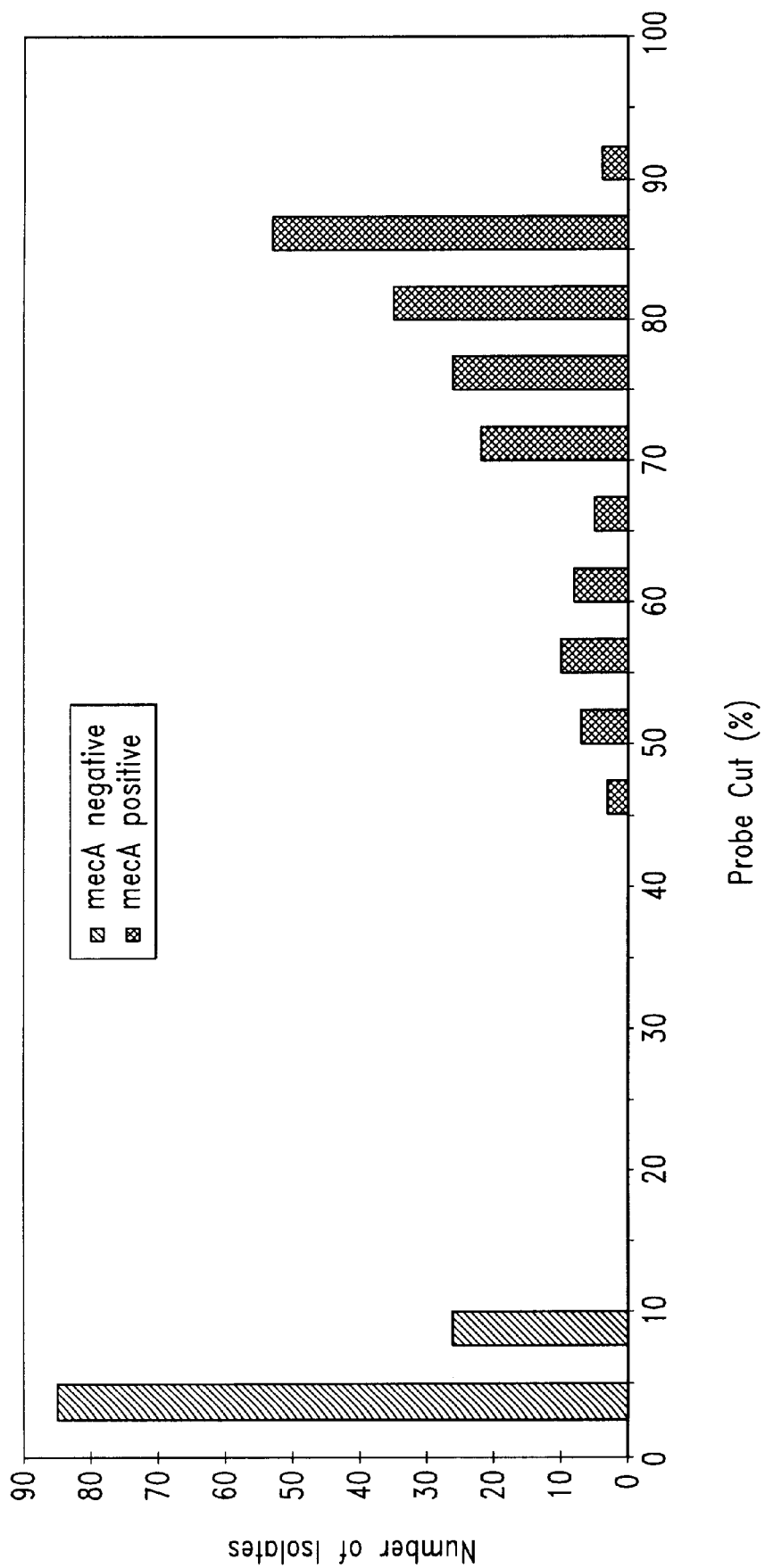
FIG. 5 depicts a histogram showing the frequency distribution results of screening 285 Staphylococcus isolates, including *S. aureus* and *S. epidermidis*, for the mecA gene from crude lysates using Cycling Probe Technology reaction. The $^{32}P$ labeled chimeric probe was mecA945-29 (SEQ ID NO:4) and the reaction mixture contained the combination of 1.0 mM EGTA and 2.0 mM spermine. The isolates can be divided into mecA positive or mecA negative based on the CPT product.

When CPT reaction results were compared to oxacillin agar screening, 4 discrepant samples were found. These isolates were observed to be agar screen positive but CPT negative. After discrepant resolution by PCR (Example 18) it was confirmed that the mecA gene was absent in these isolates. The results of the above experiment are depicted in FIG. 5 as a frequency distribution histogram of the number of isolates versus CPT product. Briefly, the frequency distribution of Percent Probe Cut separated the isolates into two distinct populations based on presence or absence of mecA gene using operator blind study.

Each of the susceptibility tests employed in this study failed to correctly identify several isolates of staphylococci. The gold standard oxacillin agar screen identified 4 S. aureus isolates as MRSA, although the mecA gene was shown not to be present. Each of these four isolates displayed borderline resistance to oxacillin (MIC's 3–16 ug/ml) and were likewise misidentified by MIC E test and oxacillin disk diffusion. One of these four isolates was further misidentified by the BBL Crystal ID MRSA System. An additional 31 S. aureus isolates lacking the mecA gene were designated as MRSA by the E test with oxacillin MIC's 3–12 ug/ml and two of these isolates were also missed by oxacillin disk diffusion. Each of these borderline oxacillin resistant S. aureus (BORSA) isolates were further shown to be susceptible to oxacillin in the presence of clavulanic acid by disk diffusion.

Conventional susceptibility tests cannot reliably differentiate between oxacillin borderline-susceptible S. aureus isolates and heterogeneously resistant MRSA isolates with low MIC.

TABLE 14

Isolates incorrectly identified by susceptibility tests

| | Isolates | | |
|---|---|---|---|
| | BORSA | MRSA | MRSE[1] |
| Total Isolates Tested | 35 | 127 | 46 |
| MIC E-Test | 35 | 0 | 4 |
| Oxacillin Agar Screen | 4 | 0 | 0 |
| Crystal MRSA ID | 1 | 4 | Not Done |
| Oxacillin Disc Diffusion | 6 | 4 | 2 |

[1]MRSE refers to methicillin resistant *Staphylococcus epidermidis*

The CPT assay accurately detected the mecA gene in S. aureus and S. epidermidis isolates and allowed for the correct identification of methicillin resistant staphylococci from methicillin susceptible staphylococci.

The above example demonstrates the sensitivity and specificity of the isotopically labeled mecA945-29 probe for the mecA gene from crude lysates of clinical staphylococcal isolates in the presence of spermine and EGTA.

Example 18

PCR Detection of mecA Gene

PCR for discrepant analysis is carried out by the following method.

Oligonucleotide primer pair mecA834-25 and mecAL1039-22 (SEQ ID NOs:6 and 7), specific for the mecA sequence of MRSA, were synthesized as described in Example 1. Crude lysates of MRSA and MSSA ATCC isolates were used as controls and PCR was performed after the hot start with the Taq polymerase.

Hot-start PCR was carried out in a 50 μl volume by adding the Taq polymerase at 80° C. after denaturation for 5 minutes at 95° C. The final PCR reaction mixture contained the following: 200 μM of each dNTP mix (Pharmacia), 1.5 mM of $MgCl_2$, 50 mM KCl, 20 mM Tris HCl, pH 8.4, (1× PCR buffer, Gibco-BRL), 0.5 μM of each primer pair, 1U of Taq DNA polymerase (Gibco-BRL) and 2 ng of Staphylococcus DNA crude lysate sample in a final reaction volume of 50 μl. Samples were cycled in the thermal cycler (PTC 100, MJ Research Inc.) using a cycle of 94° C. for 40 seconds, 53° C. for 40 seconds and 72° C. for 90 seconds. Amplification is carried out for 30 cycles.

After amplification the samples were analyzed electrophoretically using 1.8% agarose gel containing 0.5 μg/ml of ethidium bromide. A molecular weight marker was also included. The sample was considered to be positive if the 227 bp amplicon was detected. This amplicon was detected in the ATCC MRSA control but not in the ATCC MSSA control or any of the discrepent S. aureus isolates.

Example 19

Effect of Detergent as an Additive in Cycling Probe Technology and Background

The following example examines the effect of combinations of chelators, polyamines and detergents on the background and cycling in CPT reactions.

The following series of experiments (19.1 to 19.4) were carried out with CPT conditions and analysis as described in Example 14 and with the changes as noted in each experiment.

Example 19.1

In this experiment the different combinations of EGTA, spermine and detergent, DTAB (Dodecyl trimethylammonium bromide (Sigma)) were examined in CPT reaction using ARK2 (SEQ ID NO:1) probe and its synthetic complementary target ARK2-T (SEQ ID NO:2), in background of hgDNA. The reaction conditions were as follows: 3000 cpm (~1 fmol) $^{32}$P-labeled ARK2 probe, $10^{-4}$ and $10^{-5}$ pmol of complementary synthetic target ARK2-T, 1.25 mM $MgCl_2$, 4 μg RNase H (A-24), 800 ng human genomic DNA and a final reaction volume of 40 μl. The control reaction contained 0.5 mM EGTA only and the test conditions were (i) 0.5 mM EGTA with 0.5 mM, 1 mM, and 2.5 mM DTAB; (ii) 0.5 mM EGTA with 0.5 mM, 2 MM, and 5 mM spermine; and (iii) 2 mM spermine with 5 mM, 6.2 mM, and 7.5 mM DTAB. The concentration of EGTA and spermine were held constant at 0.5 mM and 2 mM as control based on results from Example 14.

TABLE 15

Use of additives EGTA, spermine and DTAB in CPT reaction using ARK2 probe (SEQ ID NO: 1) and its synthetic complementary target ARK2-T (SEQ ID NO: 2), in background of hgDNA.

| | | Probe Concentration | | | |
|---|---|---|---|---|---|
| | | $10^{-5}$ pmol | | $10^{-6}$ pmol | |
| Conditions | C4 (%) | Probe Cut (%) | Net Probe Cut (%) | Probe Cut (%) | Net Probe Cut (%) |
| 0.5 mM EGTA | 32 | 79 | 47 | 46 | 14 |
| 2.0 mM Sp + 0.5 mM EGTA | 7 | 86 | 79 | 73 | 66 |
| 0.5 mM EGTA + 2.5 mM DTAB | 15 | 67 | 52 | 32 | 17 |
| 2.0 mM Sp + 5.0 mM DTAB | 14 | 60 | 46 | 38 | 24 |

In the CPT reactions containing 800 ng of hgDNA and using the above conditions, the combination of 2 mM spermine and 0.5 mM EGTA showed the highest Net Percent Cut. The other two combinations of additives resulted in values similar to the control reaction using 0.5 mM EGTA. All the three combinations tested above resulted in greater reduction of C4 background compared to the use of 0.5 mM EGTA by itself. C4 background with the use of 2 mM spermine and 5 mM DTAB was not as low as the use of 2 mM spermine and 0.5 mM EGTA but was comparable to 0.5 mM EGTA and 2.5 mM DTAB. These results suggest that in the presence of spermine, the addition of EGTA has a relatively greater effect on reduction of C4 than the addition of DTAB. The combination of 0.5 mM EGTA and 2.5 mM DTAB resulted in the reduction of C4 background due to the addition of DTAB. This was based on the observations that in the presence of EGTA the C4 was two times greater than the combination of EGTA and DTAB. Therefore, it appears that DTAB has a similar effect on reduction of C4 as EGTA. Direct comparison between effects of EGTA and DTAB is shown in the next experiment.

The above experiment indicates that various combinations of additives can be used to reduce the background in CPT reaction due to high amount of heterologous DNA.

Example 19.2

The effect of the additives EGTA and DTAB in CPT reaction with high background of hgDNA.

The CPT reaction protocols and analysis were the same as described for Example 19.2 except that the following conditions were tested: 0.5 mM EGTA and 5 mM DTAB. The experimental results are summarized in Table 16. Table 16. Use of additives EGTA and DTAB in CPT reaction using ARK2 probe (SEQ ID NO:1) and its synthetic complementary target ARK2-T (SEQ ID NO:2), in background of hgDNA.

| | | Probe Concentration | | | |
|---|---|---|---|---|---|
| | | $10^{-5}$ pmol | | $10^{-6}$ pmol | |
| Conditions | C4 (%) | Probe Cut (%) | Net Probe Cut (%) | Probe Cut (%) | Net Probe Cut (%) |
| 0.5 mM EGTA | 30% | 77% | 47% | 44% | 14% |
| 5 mM DTAB | 30% | 87% | 57% | 61% | 31% |

These results show that the C4 values obtained with either 0.5 mM EGTA or 5 mM DTAB were similar. Therefore, these two additives appear to have the same effect on C4. The Net Probe Cut is greater in reactions with DTAB than with EGTA.

Example 19.3

The effect of the combined additives EGTA and DTAB in CPT reaction with high backgrond of hgDNA.

The CPT reaction protocols and analysis were the same as described for Example 19.1 except that the following conditions were tested: the control was 0.5 mM EGTA and the test reactions contained 0.5 mM EGTA with 2.5 mM DTAB or 3.7 mM DTAB. The experimental results are summarized in Table 17.

TABLE 17

Use of additives EGTA and DTAB in CPT reaction using ARK2 probe (SEQ ID NO: 1) and its synthetic complementary target ARK2-T (SEQ ID NO: 2), in background of hgDNA.

| | | Probe Concentration | | | |
|---|---|---|---|---|---|
| | | $10^{-5}$ pmol | | $10^{-6}$ pmol | |
| Conditions | C4 (%) | Probe Cut (%) | Net Probe Cut (%) | Probe Cut (%) | Net Probe Cut (%) |
| 0.5 mM EGTA + 2.5 mM DTAB | 18% | 79% | 61% | 34% | 16% |
| 0.5 mM EGTA + 3.7 mM DTAB | 6% | 60% | 54% | 17% | 11% |

As described above, C4 background obtained in the presence of 0.5 mM EGTA is two times higher than the one obtained with 0.5 mM EGTA+2.5 mM DTAB (see example no. 1). Although Net Percent Probe Cut was previously very similar when using EGTA or EGTA+DTAB, in this experiment, the Net Percent Probe Cut seems slightly better in the presence of EGTA+DTAB than the one obtained with EGTA (i.e. compare Net Percent Probe Cut at $10^{-6}$ pmol, 16% and 4%). In the presence of 0.5 mM EGTA and higher concentration of DTAB (i.e. 3.7 mM), C4 background was reduced to 6% which is additional 50% reduction comparing to the C4 obtained with 0.5 mM EGTA and 2.5 mM DTAB. With 0.5 mM EGTA and 3.7 mM DTAB, the Net Percent Probe Cut remains similar to the one obtained with lower concentration of DTAB (i.e. compare Net Percent Probe Cut at $10^{-6}$ pmol, 16% and 11%).

Addition of detergent DTAB to chelator EGTA results in reduction of C4 background while the Net Percent Probe Cut remains unchanged. In the presence of 0.5 mM EGTA, 3.7 mM DTAB appears to be better than the lower concentration of DTAB (i.e. 2.5 mM).

Example 19.4

The effect of the combined additives DTAB and spermine in CPT reaction with high background of hgDNA is examined.

The CPT reaction protocols and analysis were the same as described for Example 19.1 except that the following conditions were tested: the control reaction contained 5 mM DTAB and the test reactions were 5 mM DTAB with 2 mM spermine or 5 mM spermine. The experimental results are summarized in Table 18.

TABLE 18

Use of additives DTAB and spermine in CPT reaction using ARK2 probe (SEQ ID NO: 1) and its synthetic complementary target ARK2-T (SEQ ID NO: 2), in background of hgDNA.

| | | Probe Concentration | | | |
|---|---|---|---|---|---|
| | | $10^{-5}$ pmol | | $10^{-6}$ pmol | |
| Conditions | C4 (%) | Probe Cut (%) | Net Probe Cut (%) | Probe Cut (%) | Net Probe Cut (%) |
| 5 mM DTAB | 31% | 87% | 56% | 54% | 23% |
| 5 mM DTAB + 2 mM Spermine | 22% | 91% | 69% | 43% | 21% |
| 5 mM DTAB + 5 mM Spermine | 14% | 88% | 74% | 38% | 24% |

From the above results the control condition with 5 mM DTAB resulted in similar C4 background and maybe slightly better Net Percent Cut than what is usually seen with 0.5 mM EGTA (see example nos. 1, 2, and 3). Addition of spermine to the reaction containing 5 mM DTAB was beneficial since the Net probe cut remains the same while C4 background was reduced.

Under the above conditions DTAB appears to function similarly to 0.5 mM EGTA. Addition of polyamine spermine to detergent DTAB reduced C4 background while the Net Probe Cut stayed the same. Increasing the concentration of spermine with DTAB resulted in improvement of the Net Percent Cut in CPT.

Example 20
Possible Mechanism of Additive Spermine in Reduction of C4 Background The following example examines the possible mechanism of spermine on reduction of background due to heterologous DNA in CPT reaction.

Figure 6:
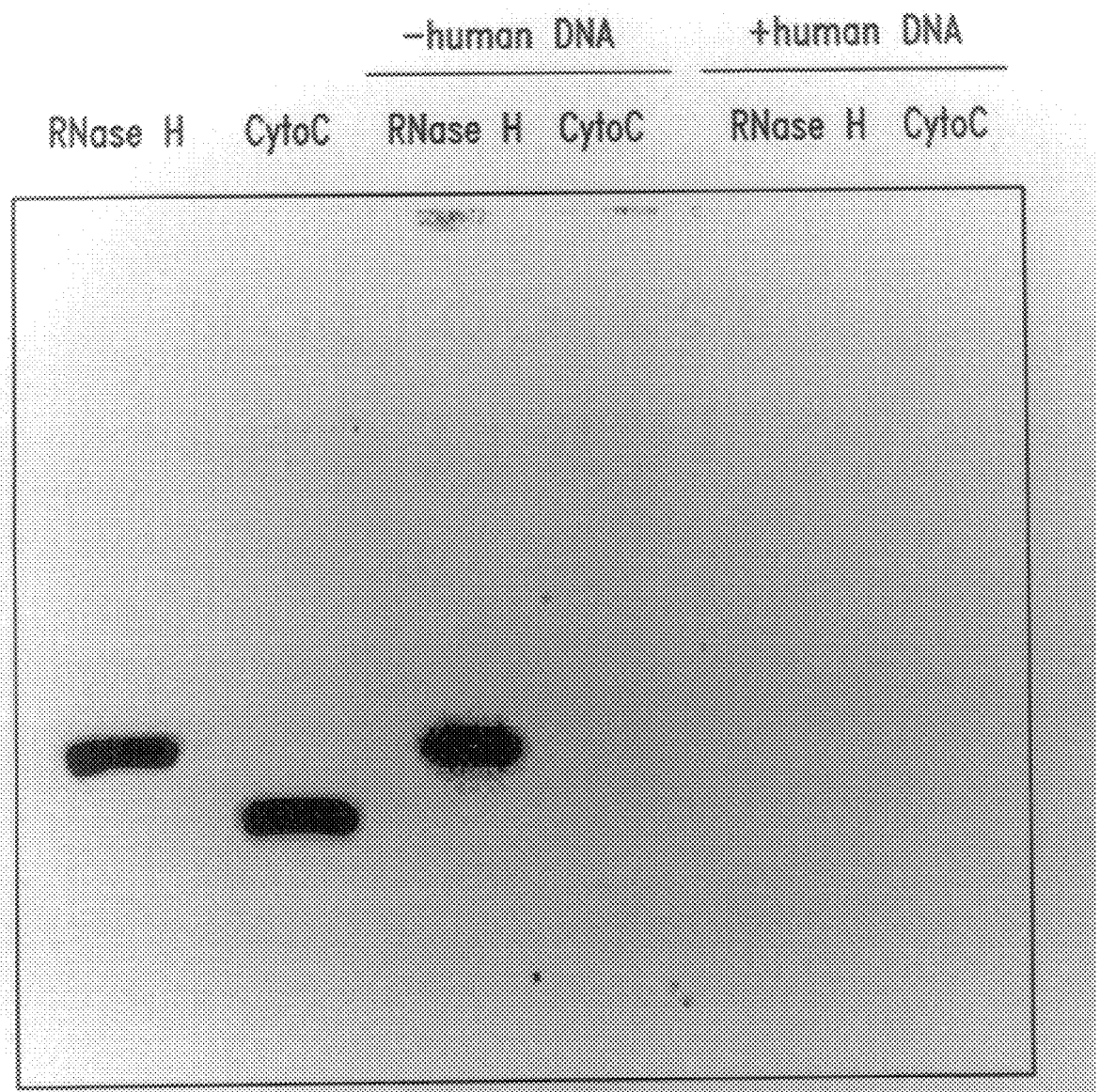
FIG. 6 shows the results of the membrane binding assay examining the binding of RNase H and to the ARK2 (SEQ ID NO:1) probe in background of human genomic DNA (hgDNA). In the absence of hgDNA RNase H binds the probe, however in the presence of hgDNA, this interaction was shown to be disrupted. Binding of the control, Cytochrome C (CytoC), to ARK2 probe was neither observed in the absence or presence of hgDNA.

To gain a better understanding of how the presence of non-homologous DNA interferes with the CPT reaction, the interactions between two CPT components, chimeric ARK2 probe and RNase H were examined. A membrane binding assay was used to qualitatively assess the binding of chimeric probe and RNase H either in the presence or absence of hgDNA. Amounts of RNase H, probe and hgDNA used for membrane binding studies were similar to those used for CPT in Example 14. FIG. 6 shows the results of the binding assay. It was observed that the binding of RNase H and probe was detected in the absence of hgDNA however, in the presence of hgDNA, the RNase H-probe interaction was disrupted (FIG. 6). Cytochrome C was used as a control protein for the membrane binding assay since its pI is similar to pI of RNase H. Binding of Cytochrome C to ARK2 probe was not observed either in the absence or presence of hgDNA.

Figures 7A, 7B:
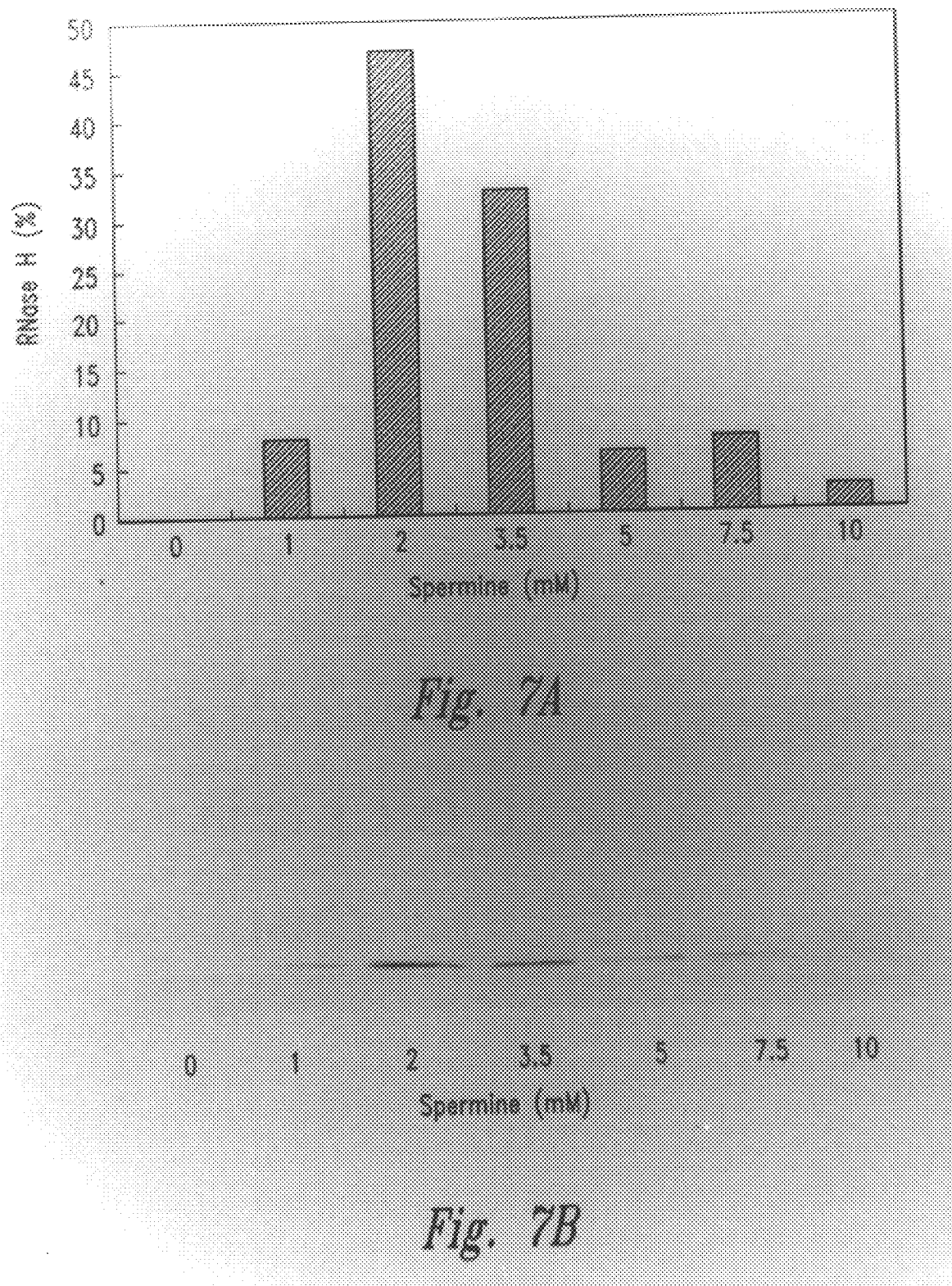
FIGS. 7A and 7B are histograms that depict the results from the elution profile of the RNase H from single-stranded DNA agarose column. The relative amount of RNase H eluted with the increasing concentration of spermine (FIG. 7A) were estimated from Western Blot (FIG. 7B). Two percent of the RNase H loaded onto the column was eluted in the flowthrough fraction.

In order to examine whether hgDNA may compete with the probe for RNase H binding if such an interaction between RNase H and non-homologous DNA exists, a ss DNA-agarose column was utilized in combination with western blot analysis. Briefly, after passing the enzyme through a ss DNA-agarose column, semiquantitative analysis showed the presence of approximately 2% of RNase H in the flowthrough, indicating that the majority of RNase H was bound to the ss DNA. Approximately 98% of the bound RNase H was eluted from the DNA-agarose column by increasing the concentration of spermine as detected by western blot analysis (FIG. 7). The highest percentage of the enzyme was eluted with 2 mM spermine, the same spermine concentration determined to be optimal for the CPT reaction. The binding of RNase H was specific to DNA since 80% of the enzyme was detected in the flow-through when using an agarose column without any DNA (data not shown).

Figures 8A, 8B:
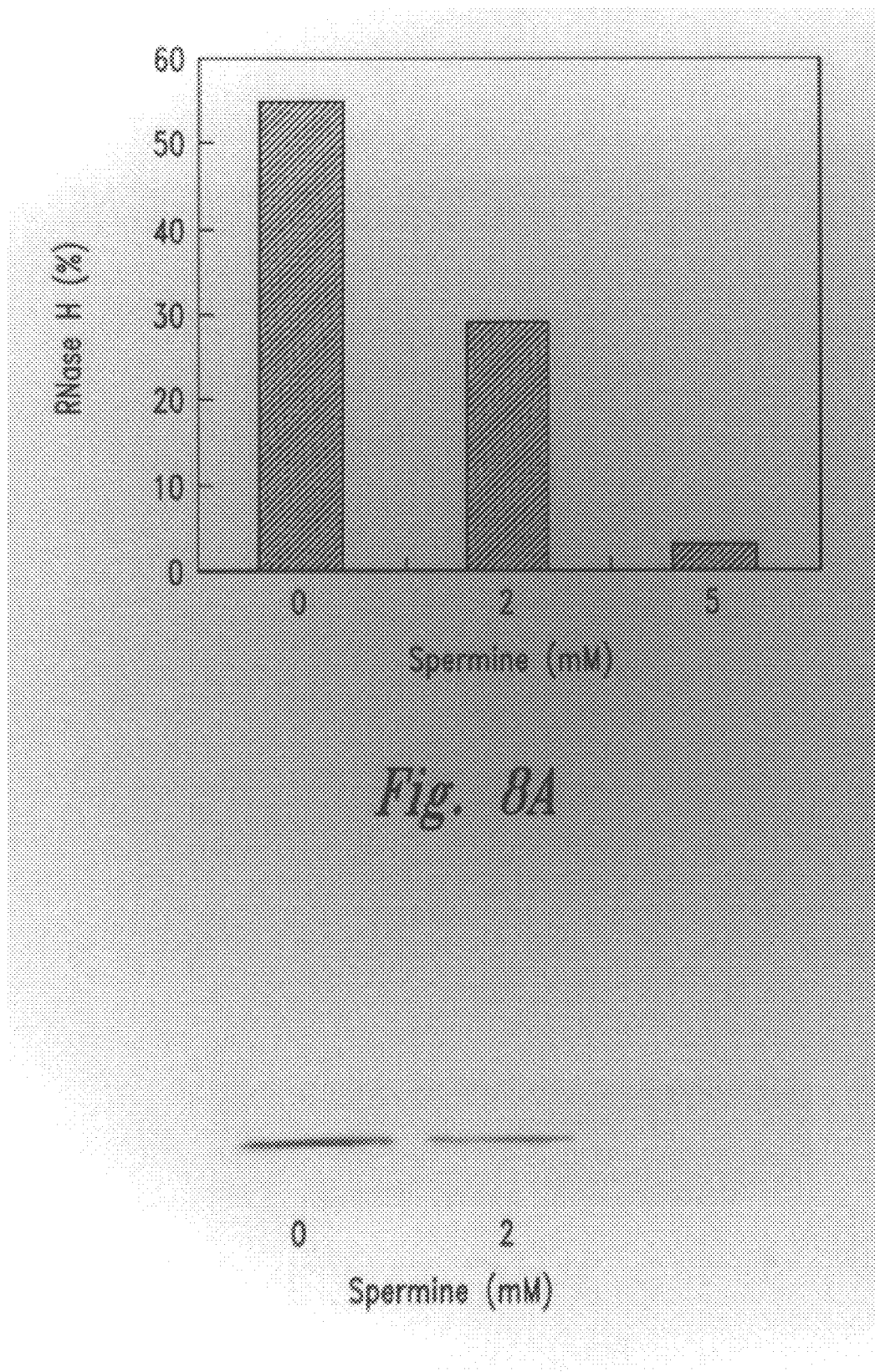
FIGS. 8A and 8B are histograms that depict the results from the elution profile of RNase H from single-stranded DNA agarose column equilibrated with 2 mM spermine. The relative amount of RNase H eluted with the increasing concentration of spermine (FIG. 8A) were estimated from Western Blot (FIG. 8B). The fraction indicated by 0 mM of spermine includes the flowthrough of RNase H obtained during the loading of the RNase H onto the column.

To determine if binding of spermine to ss DNA within the agarose column was responsible for displacement of RNase H, a ssDNA-agarose column pre-equilibrated with 2 mM spermine was used. After passing the enzyme through, semiquantitative analysis demonstrated that more than 50% of RNase H did not interact with the column (FIG. 8). The majority of bound RNase H was eluted from the column with 2 mM spermine whereas a relatively insignificant amount of RNase H was detected in the following elution using 5 mM spermine. This data indicated that both RNase H and spermine compete for binding of ss DNA and moreover, that 2 mM spermine is sufficient to displace RNase H from ss DNA. A similar principle, displacement of RNase H from DNA by spermine, may account for improvement of the CPT in the presence of non-homologous DNA. For example, within the CPT reaction, due to RNase H binding to hgDNA, less RNase H is available for target-mediated probe cleavage and thus lower amount of Percent Probe Cut is generated. Addition of spermine to such a reaction, based on DNA-agarose column data, would reduce the non-specific interaction between RNase H and hgDNA, thus, increasing the specific probe cleavage or amount of CPT product.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for detecting a target nucleic acid molecule, comprising:

(a) reacting a mixture comprising (i) a target nucleic acid molecule; (ii) a single-stranded nucleic acid probe containing a scissile linkage; (iii) an enzyme capable of cleaving the probe portion of a double-stranded target-probe complex at the scissile linkage; and (iv) ribosomal protein, under conditions and for a time sufficient to allow said target nucleic acid and said probe to hybridize to each other and form a double-stranded target-probe complex, followed by cleavage of the probe and cycling of the target to a new uncleaved probe, such that one or more portions of said cleaved nucleic acid probe are released from said target-probe complex; and (b) determining whether cleaved portions of said nucleic acid probe are produced, thereby detecting the presence of said target nucleic acid.

2. A method for detecting a target nucleic acid molecule, comprising:
(a) reacting a mixture comprising (i) a target nucleic acid molecule; (ii) a single-stranded nucleic acid probe containing a scissile linkage; (iii) an enzyme capable of cleaving the probe portion of a double-stranded target-probe complex at the scissile linkage; and (iv) spermine, under conditions and for a time sufficient to allow said target nucleic acid and said probe to hybridize to each other and form a double-stranded target-probe complex, followed by cleavage of the probe and cycling of the target to a new uncleaved probe, such that one or more portions of said cleaved nucleic acid probe are released from said target-probe complex; and
(b) determining whether cleaved portions of said nucleic acid probe are produced, thereby detecting the presence of said target nucleic acid.

3. The method according to claim 1 wherein the step of determining comprises detecting a decrease in the amount of uncleaved probe.

4. The method according to claim 1 wherein the step of determining comprises directly determining cleaved portions of the nucleic acid probe.

5. The method according to claim 1 or 2 wherein said probe comprises the structure $[NA_1\text{-}S\text{-}NA_2]_n$, and wherein $NA_1$ and $NA_2$ are nucleic acid sequences composed of DNA.

6. The method according to claim 5 wherein when S is an RNA sequence.

7. The method according to claim 1 or 2 wherein said enzyme is Rnase H.

8. The method according to claim 7 wherein said RNase H is thermostable RNase H.

9. The method according to claim 7 wherein said RNase H is non-thermostable RNase H.

10. The method according to claim 1 wherein said ribosomal protein is a prokaryotic ribosomal protein.

11. The method according to claim 1 wherein said ribosomal protein is a eukaryotic ribosomal protein.

12. The method according to claim 8 wherein said ribosomal protein is S19 or L34 ribosomal protein.

13. The method according to claim 1 wherein said reaction mixture further comprises spermine.

14. The method according to claim 2 wherein said reaction mixture further comprises a chelator.

15. The method according to claim 14 wherein said chelator is EGTA or EDTA.

16. The method according to claim 1 or 2 wherein said probe is labeled directly or indirectly with a detectable marker.

17. The method according to claim 2 wherein said reaction mixture further comprises a Magnesium ion.

* * * * *

SEQUENCE LISTING

<160> NUMBER OF SEQ ID NOS: 11

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence:  Product of Solid Phase Synthesis

<400> SEQUENCE: 1
gtcgtcagac ccaaaacccc gagaggg                                          27

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Product of
      Solid Phase Synthesis

<400> SEQUENCE: 2
ccctctcggg gttttgggtc tgacgac                                          27

<210> SEQ ID NO 3
<211> LENGTH: 95
<212> TYPE: DNA
<213> ORGANISM: Artificial Sequence
<220> FEATURE:
<223> OTHER INFORMATION: Description of Artificial Sequence: Product of
      Solid Phase Synthesis

<400> SEQUENCE: 3
atacgactca ctatagggaa ttcgagctcg gtacccctct cggggttttg ggtctgacga      60
ctgcaggcat gcaagcttgg cactggccgt cgttt                                 95

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Product of
      Solid Phase Synthesis

<400> SEQUENCE: 4
aatagagaaa aagaaaaaag atggcaaag                                        29

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Product of
      Solid Phase Synthesis

<400> SEQUENCE: 5
ctttgccatc ttttttcttt ttctctatt                                        29

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Product of
      Solid Phase Synthesis

<400> SEQUENCE: 6
tggtaaaaag ggactcgaaa aactt                                            25

<210> SEQ ID NO 7
<211> LENGTH: 22
<212> TYPE: DNA
<213> ORGANISM: Artificial Sequence
<220> FEATURE:

```
<223> OTHER INFORMATION: Description of Artificial Sequence: Product of
      Solid Phase Synthesis

<400> SEQUENCE: 7
ggtggatagc agtacctgag cc                                                    22

<210> SEQ ID NO 8
<211> LENGTH: 21
<212> TYPE: PRT
<213> ORGANISM: Thermus thermophilus
<220> FEATURE:
<221> NAME/KEY: MOD_RES
<222> LOCATION: (1)
<223> OTHER INFORMATION: Where Xaa is an unidentified amino acid residue
<220> FEATURE:
<221> NAME/KEY: MOD_RES
<222> LOCATION: (16)
<223> OTHER INFORMATION: Where Xaa is an unidentified amino acid residue

<400> SEQUENCE: 8

Xaa Lys Arg Thr Phe Gln Pro Ser Val Leu Lys Arg Asn Arg Ser Xaa
 1               5                  10                  15

Gly Phe Arg Ala Arg
            20

<210> SEQ ID NO 9
<211> LENGTH: 21
<212> TYPE: PRT
<213> ORGANISM: Escherichia coli

<400> SEQUENCE: 9

Met Lys Arg Thr Phe Gln Pro Ser Val Leu Lys Arg Asn Arg Ser His
 1               5                  10                  15

Gly Phe Arg Ala Arg
            20

<210> SEQ ID NO 10
<211> LENGTH: 18
<212> TYPE: PRT
<213> ORGANISM: Thermus thermophilus

<400> SEQUENCE: 10

Arg Ser Leu Ala Gly Gly Pro Phe Ile Asp Leu His Leu Ile Lys Lys
 1               5                  10                  15

Val Glu

<210> SEQ ID NO 11
<211> LENGTH: 18
<212> TYPE: PRT
<213> ORGANISM: Escherichia coli

<400> SEQUENCE: 11

Arg Ser Leu Lys Lys Gly Pro Phe Ile Asp Leu His Leu Leu Lys Lys
 1               5                  10                  15

Val Glu
```